US006867179B1

(12) United States Patent
Gilchrest et al.

(10) Patent No.: US 6,867,179 B1
(45) Date of Patent: Mar. 15, 2005

(54) METHODS OF INDUCING HAIR GROWTH AND COLORATION

(75) Inventors: Barbara A. Gilchrest, Boston, MA (US); Mina Yaar, Sharon, MA (US); Mark Eller, Boston, MA (US)

(73) Assignee: Trustees of Boston University, Boston, MA (US)

( * ) Notice: Subject to any disclaimer, the term of this patent is extended or adjusted under 35 U.S.C. 154(b) by 406 days.

(21) Appl. No.: 09/632,748

(22) Filed: Aug. 4, 2000

Related U.S. Application Data

(63) Continuation of application No. PCT/US99/02362, filed on Feb. 3, 1999, which is a continuation-in-part of application No. 09/018,194, filed on Feb. 4, 1998, which is a continuation-in-part of application No. 08/793,683, filed on Apr. 3, 1997, now abandoned, which is a continuation of application No. 08/298,941, filed on Aug. 31, 1994, now Pat. No. 6,103,689.

(51) Int. Cl.⁷ ........................ A61K 38/08; A61K 38/17; A61K 38/18
(52) U.S. Cl. ............................ 514/2; 514/12; 514/17; 514/15
(58) Field of Search ............................ 514/2, 12, 17, 514/15

(56) References Cited

U.S. PATENT DOCUMENTS

| | | | |
|---|---|---|---|
| 4,621,023 A | 11/1986 | Redziniak et al. | |
| 5,077,211 A | 12/1991 | Yarosh | |
| 6,242,416 B1 | 6/2001 | Gilchrest et al. | |

FOREIGN PATENT DOCUMENTS

| | | |
|---|---|---|
| EP | 0 584 452 A1 | 3/1994 |
| JP | 63183518 | 7/1988 |
| JP | 63301810 | 12/1988 |
| JP | 11 029441 A | 2/1999 |
| WO | WO 92/18149 | 10/1992 |
| WO | WO 95/21193 | 8/1995 |
| WO | WO 96/06633 | 3/1996 |
| WO | WO 96/12955 | 5/1996 |
| WO | WO 97/37228 | 10/1997 |

OTHER PUBLICATIONS

Zhai, S., et al., "A Role for P75 Nerve Growth Factor Receptor in Programmed Melanocyte Cell Death After Injury and With Aging," *Journal of Investigative Dermatology*, 102(4):545, SID Abstract #131 (1994).

Yaar, M., et al., "Cloning and Expression of a Novel Nerve Growth Factor Related Molecule in Human Skin," *Journal of Investigative Dermatology*, 100:(4):548, Abstract #100 (1993).

Yaar, M., et al., "Melanocyte Function in Human Skin is Modulated by Neurotrophic Factors through TRK Receptors," *Journal of Investigative Dermatology*, 100(4):511, Abstract #134 (1993).

Zhai, S., et al., "Nerve Growth Factor (NGF) Enhances Survival of Human Melanocytes," *Journal of Investigative Dermatology*, 101:434, Abstract #279 (1993).

Yaar, M., et al., "Involvement of TRK Proto–Oncogene in Physiologic Stimuli of Human Melanocytes," *Clinical Research*, 40(2):531A, SID Abstracts, (1992).

Price, V.H., "Alopecia Areata: Clinical Aspects," *Journal of Investigative Dermatology*, 96(5), Supplement:68S (19991).

Yaar, M., et al., "Human Melanocyte Growth and Differentiation: A Decade of New Data," *Journal of Investigative Dermatology*, 97(4):611–617 (1991).

Goldsmith, L.A., "Summary of Alopecia Areata Research Workshop and Future Research Directions," *Journal of Investigative Dermatology*, 96(5), Supplement:98S–100S (1991).

Friedmann, P.S., "Clinical and Immunologic Associations of Alopecia Areata," *Seminars in Dermatology*, 4(1):9–15 (1985).

Stenn, K.S., et al., "Expressing of the bcl–2 Protooncogene in the Cycling Adult Mouse Hair Follicle," *Journal of Investigative Dermatology*, 103(1):107–111 (1994).

Rabizadeh, S., et al., "Induction of Apoptosis by the Low–Affinity NGF Receptor," *Science*, 261:345–348 (1993).

Garcia, I., et al., "Prevention of Programmed Cell Death of Sympathetic Neurons by the bcl–2 Proto–Oncogene," *Science*, 258:302–304 (1992).

Allsopp, T.E., et al., "The Proto–Oncogene bcl–2 Can Selectively Rescue Neurotrophic Factor–Dependent Neurons from Apoptosis," *Cell*, 73:295–307 (1993).

Veis, D.J., et al., "Bcl–2–Deficient Mice Demonstrate Fulminant Lymphoid Apoptosis, Polycystic Kidneys, and Hypopigmented Hair," *Cell* 75:229–240 (1993).

DiMarco, E., et al., "Growth–regulated Synthesis and Secretion of Biologically Active Nerve Growth Factor by Human Keratinocytes," *Journal of Biological Chemistry*, 266(32):21718–21722 (1991).

Yaar, M., et al,. "Evidence for Nerve Growth Factor–mediated Paracrine Effects in Human Epidermis," *Journal of Cell Biology* 115(3):821–828 (1991).

Barinaga, M., "Death Gives Birth to the Nervous System. But How?" *Science*, 259:762–763 (1993).

(List continued on next page.)

Primary Examiner—Gary Kunz
Assistant Examiner—Stephen Gucker
(74) *Attorney, Agent, or Firm*—Hamilton, Brook, Smith & Reynolds, P.C.

(57) ABSTRACT

Methods to control, or manipulate, melanocyte and keratinocyte cell death are disclosed. In particular, a method of preventing epidermal melanocyte cell loss due to injury in a vertebrate is disclosed. Also disclosed is a method of inducing hair growth in a vertebrate, a method of inducing hair color in a vertebrate, a method of inducing skin color in a vertebrate, a method of treating baldness in an individual, and a method of treating alopecia areata in an individual.

8 Claims, 17 Drawing Sheets

OTHER PUBLICATIONS

Hockenbery, D.M., et al., "Bcl–2 Functions in an Antioxidant Pathway to Prevent Apoptosis," *Cell*, 75:241–251 (1993).

Di Marco, E., et al., "Molecular Cloning of trkE, a Novel trk–related Putative Tyrosine Kinase Receptor Isolated from Normal Human Keratinocytes and Widely Expressed by Normal Human Tissues," *Journal of Biological Chemistry*, 268(32):24290–24295 (1993).

Peacocke, M., et al., "Induction of nerve growth factor receptors on cultured human melanocytes," *Proc. Natl. Acad. Sci. USA*, 85:5282–5286 (1988).

Barinaga, M., "Cell Suicide: By ICE, Not Fire," *Science*, 263:754–756 (1994).

Paus, R., et al., "Telogen skin contains an inhibitor of hair growth," *British Journal of Dermatology*, 122:777–784 (1990).

Ross, A.H., et al., "Characterization of nerve growth factor receptor in neural crest tumors using monoclonal antibodies," *Proc. Natl. Acad. Sci. USA*, 81:6681–6685 (1984).

Halaban, R., et al., "Basic Fibroblast Growth Factor from Human Keratinocytes Is A Natural Mitogen for Melanocytes," *Journal of Cell Biology*, 107:1611–1619 (1988).

Halaban, R., et al., "bFGF is the Putative Natural Growth Factor For Human Melanocytes," *In Vitro Cellular & Development Biology*, 23(1):47–52 (1987).

Ullrich, A., et al., "Human β–nerve growth factor gene sequence highly homologous to that of mouse," *Nature*, 303:821–825 (1983).

Morgenstern, J.P., et al., "Advanced mammalian gene transfer: high titre retroviral vectors with multiple drug selection markers and a complementary helper–free packaging cell line," *Nucleic Acids Research*, 18(12):3587–3596 (1990).

Johnson, D., et al., "Expression and Structure of the Human NGF Receptor," *Cell*, 47:545–554 (1986).

Heuer, J.G., et al., Structure and Development Expression of the Chicken NGF Receptor, *Development Biology*, 137:287–304 (1990).

Large, T.H., et al., "Structure and Developmental Expression of the Nerve Growth Factor Receptor in the Chicken Central Nervous System," *Neuron*, 2:1123–1134 (1989).

Radeke, M.J., et al., "Gene transfer and molecular cloning of the rat nerve growth factor receptor," *Nature*, 325:593–597 (1987).

Mitchell, A.J., et al., "Alopecia areata: Pathogenesis and treatment," *Journal of the American Academy of Dermatology*, 11(5)1:763–775 (1984).

Klein, R., et al., "The trk Proto–Oncogene Encodes a Receptor for Nerve Growth Factor," *Cell*, 65:189–197 (1991).

Maisonpiere, P.C., et al., "Neurotrophin–3: A Neurotrophic Factor Related to NGF and BDNF," *Science*, 247:1446–1451 (1990).

Chao, M.V., et al., "Gene Transfer and Molecular Cloning of the Human NGF Receptor," *Science*, 232:518–521 (1986).

Headington, J.T., "Transverse Microscopic Anatomy of the Human Scalp," *Arch. Dermatol.*, 120:449–456 (1984).

Sperling, L.C., "Hair anatomy for the children," *Journal of the American Academy of Dermatology*, 25(1):1–17 (1991).

Gilchrest, B.A., "Skin and Aging Processes," (Boca Raton, FL., *CRC Press, Inc.*) pp. 19–20 (1984).

Bertolino, A.P., et al., "Biology of Hair Follicles,In *Dermatology in General Medicine*," Thomas B Fitzpatrick et al. (Ed.), Section 4, Chapter 19, (NY: McGraw–Hill, Inc.) pp. 289–293, Fourth Edition, (1993).

Bertolino, A.P., et al., "Hair," In *Dermatology in General Medicine*, Thomas B. Fitzpatrick et al. (Ed.), Section 10, Chapter 61, (NY: McGraw–Hill, Inc.) pp. 671–673, Fourth Edition, (1993).

Marchetti, D., et al, "Nerve Growth Factor Effects on Human and Mouse Melanoma Cell Invasion and Heparanase Production," *Int. J. Cancer*, 55:692–699 (1993).

Spritz, R.A., et al., "Inhibition of Proliferation of Human Melanocytes by a KIT Antisense Oligodeoxynucleotide: Implications for Human Piebaldism and Mouse Dominant White Spotting (W)," *J. Invest. Dermatology*, 103(2):148–150 (1994).

Nataraj, A., et al., "bcl–2 Oncogene Blocks Differentiation and Extends Viability But Does Not Immortalize Normal Human Keratinocytes," *Intl. J. Oncology*, 4:1211–1218 (1994).

Nakayama, K., et al., "Targeted Disruption of Bcl2αβ in Mice: Occurrence of Gray Hair, Polycystic Kidney Disease, and Lymphocytopenia," *Proc. Natl. Acad. Sci. USA*, 91:3700–3704 (1994).

Ibáñez. C. F. , et al., "Disruption of the Low Affinity Receptor–Binding Site of NGF Allows Neuronal Survival and Differentiation by Binding to the trk Gene Product," *Cell*, 69:329–341 (1992).

Lu, K., et al., "Ras Proteins are Essential and Selective for the Action of Insulin–Like Growth Factor 1 Late in the $G_1$ Phase of the Cell Cycle in BALB/c Murine Fibroblasts," *Proc. Natl. Acad. Sci. USA*, 89:3889–3893 (1992).

Yaar, M., et al., "Human Nevocellular Nevus Cells are Surrounded by Basement Membrane Components," *Laboratory Invest.*, 58(2):157–162 (1998).

Tsujimoto, Y., et al., "Analysis of the Structure, Transcripts, and Protein Products, of bcl–2, the Gene Involved in Human Follicular Lymphoma," *Proc. Natl. Acad. Sci. USA*, 83:5214–5218 (1986).

International Search Report, International Application No.: PCT/US97/04966, mailed Aug. 28, 1997.

Yaar, M., et al., "The trk Family of Receptors Mediates Nerve Growth Factor and Neurotrophin–3 Effects in Melanocytes," *J. Clin. Invest.*, 94:1550–1562 (1994).

Lapchak, P.A., "Nerve Growth Factor Pharmacology: Application to the Treatment of Cholinergic Neurodegeneration in Alzheimer's Disease," *Exper. Neurology*, 124:16–20 (1993).

Casaccia–Bonnefil, P., et al., "Death of Oligodendrocytes Mediated by the Interaction of Nerve Growth Factor With its Receptor p75," *Nature*, 383:716–719 (1996).

Huber, L.J., et al., "A Potential Interaction of p75 and trkA NGF Receptors Revealed by Affinity Crosslinking and Immunoprecipitation," *J. Neuroscience Res.*, 40:557–563 (1995).

Mahadeo, D., et al., "High Affinity Nerve Growth Factor Binding Displays a Faster Rate of Association Than $p140^{trk}$ Binding," *J. Biol. Chem.*, 269(9):6884–6891 (1994).

Frade, J.M., et al., "Induction of Cell Death by Endogenous Nerve Growth Factor Through its p75 Receptor," *Nature*, 383:166–168 (1996).

Reams, W.H., "Effects of Nerve–Growth Promoting Protein on Murine Integument," *J. Invest. Dermatology*, 49(6):552–558 (1967).

Zhai, S., et al., "The Role of Nerve Growth Factor in Preventing Keratinocyte Apoptosis," Abstract No. 108, *J. Invest. Dermat.*, 104:572 (1995).

Cotman, C.W., et al., "A Potential Role for Apoptosis in Neurodegeneration and Alzheimer's Disease," *Mol. Neurobiol.*, 10:19–45 (1995).

Su, J.H., et al., "Immunohistochemical evidence for apoptosis in Alzheimer's disease," *Neuroreport*, 5(18):2529–2533 (1994).

Oltvai, Z.N., et al., "Bcl–2 Heterodimerizes In Vivo with a Conserved Homolog, Bax, That Accelerates Programmed Cell Death," *Cell*, 74:609–619 (1993).

Lärkfors, L., et al., "Decreased level of nerve growth factor (NGF) and its messenger RNA in the aged rat brain," *Molecular Brain Res.*, 3:55–60 (1987).

Botchkarev, V.A., "New Roles for Neurotrophin–3, Neurotrophin–4 and Brain Derived Neurotrophic Factor: Involvement in Hair Growth Control," *J. Invest. Dermatol.*, 110(4):48, Abstract #51 (1998).

Botchkarev, V.A., et al., "Neurotrophin–3 Involvement in the Regulation of Hair Follicle Morphogensis," *J. Invest. Dermatol.*, 111(2):279–285 (1998).

Paus, R., et al., "Nerve growth factor modulates keratinocyte proliferation in murine skin organ culture," *Brit. J. Dermatol.*, 130:174–180 (1994).

Paus, R., et al., "Neural Mechanisms of Hair Growth Control," JID Symposium, 2(1):61–68 (Aug. 1997).

Yaar, M., et al., "Human Melanocytes as a Model System for Studies of Alzheimer Disease," *Arch. Dermatol.*, 133:1287–1291 (1997).

Zhai, S., et al., "Activation of p75 nerve growth factor receptor is blocked by cyclic peptides containing a lysine–g-lycine–alanine (KGA) motif," *Jour. of Investigative Dermatology*, 110(4):481 (1998).

Botchkarev, V.A., et al., "A New Role for Neurotrophin–3; Involvement in the Regulation of Hair Follicle Regression (Catagen)," *American Journal of Pathology*, 153(3):785–799 (1998).

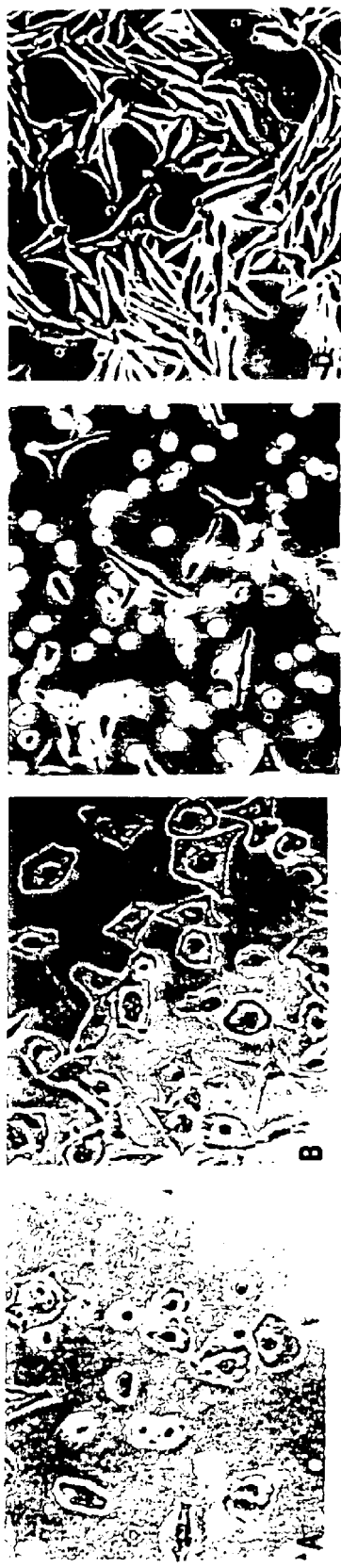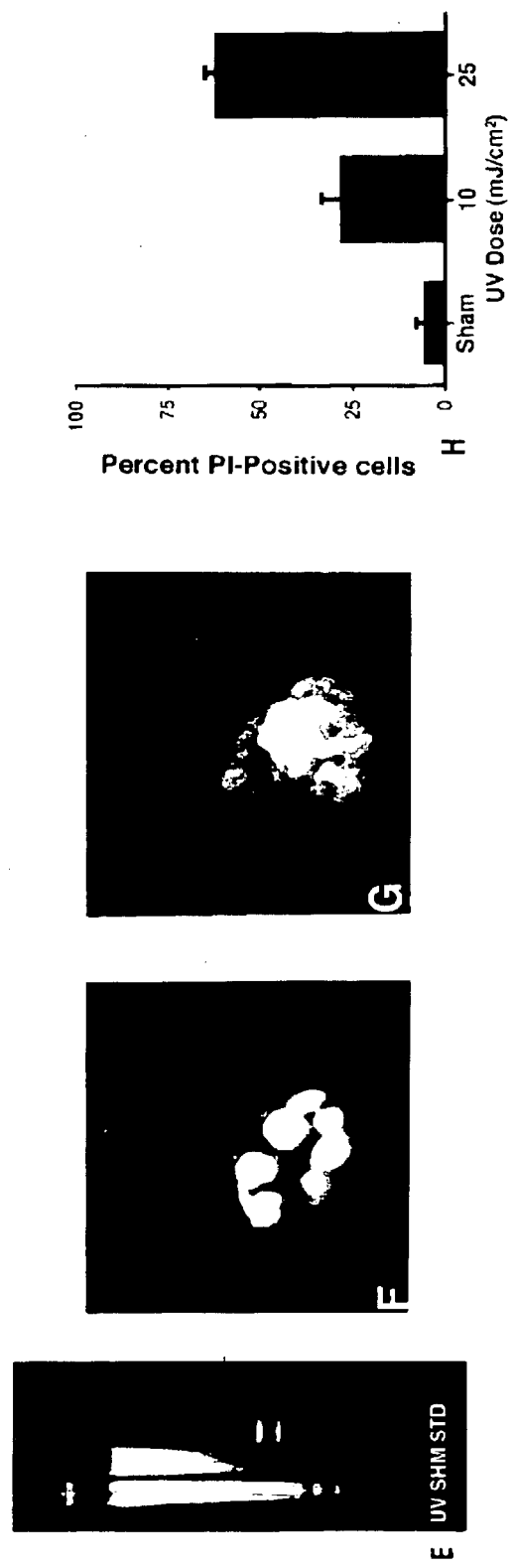

FIG. 2F
FIG. 2G
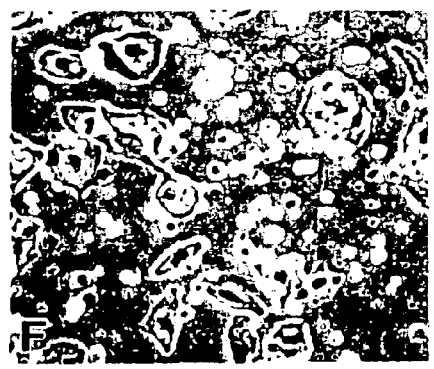
FIG. 2H
FIG. 2I

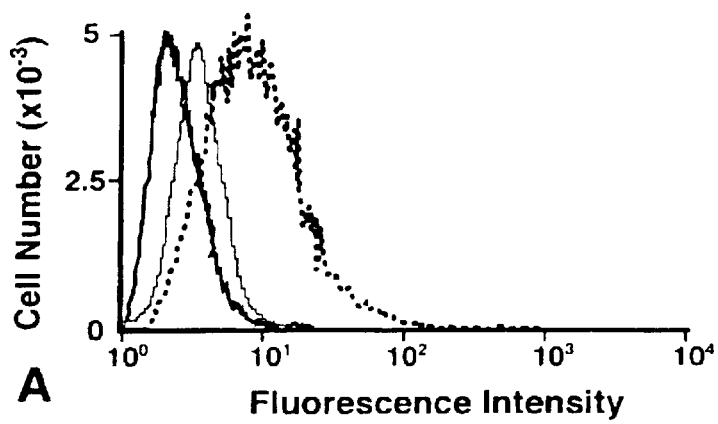
FIG. 4A
FIG. 4B
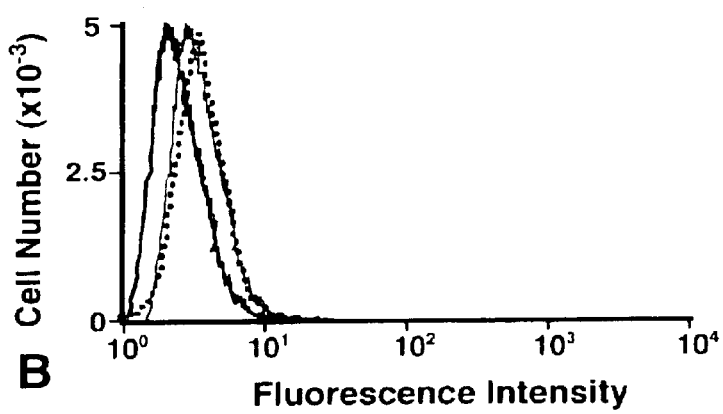
FIG. 4C

SEQUENCE LISTING

```
<160> NUMBER OF SEQ ID NOS:  11

<210> SEQ ID NO 1
<211> LENGTH: 8
<212> TYPE: PRT
<213> ORGANISM: Homo sapiens

<400> SEQUENCE: 1

Val Gly Ser Asn Lys Gly Ala Ile
1               5

<210> SEQ ID NO 2
<211> LENGTH: 8
<212> TYPE: PRT
<213> ORGANISM: Homo sapiens

<400> SEQUENCE: 2

Thr Asp Ile Lys Gly Lys Glu Val
1               5

<210> SEQ ID NO 3
<211> LENGTH: 5
<212> TYPE: PRT
<213> ORGANISM: Artificial Sequence
<220> FEATURE:
<223> OTHER INFORMATION: Pentapeptide

<400> SEQUENCE: 3

Cys Lys Gly Ala Cys
1               5

<210> SEQ ID NO 4
<211> LENGTH: 10
<212> TYPE: PRT
<213> ORGANISM: Artificial Sequence
<220> FEATURE:
<223> OTHER INFORMATION: Cyclic peptide

<400> SEQUENCE: 4

Cys Val Gly Ser Asn Lys Gly Ala Ile Cys
1               5                   10

<210> SEQ ID NO 5
<211> LENGTH: 19
<212> TYPE: DNA
<213> ORGANISM: Homo sapiens

<400> SEQUENCE: 5
ggcacctgcc cccatcgcc                                                     19

<210> SEQ ID NO 6
<211> LENGTH: 19
<212> TYPE: DNA
<213> ORGANISM: Artificial Sequence
```

```
<220> FEATURE:
<223> OTHER INFORMATION: Nonsense oligonucleotide

<400> SEQUENCE: 6
ctcccactcg tcattcgac                                           19

<210> SEQ ID NO 7
<211> LENGTH: 19
<212> TYPE: DNA
<213> ORGANISM: Homo sapiens

<400> SEQUENCE: 7
cccagcgtgc gccatcctt                                           19

<210> SEQ ID NO 8
<211> LENGTH: 19
<212> TYPE: DNA
<213> ORGANISM: Artificial Sequence
<220> FEATURE:
<223> OTHER INFORMATION: Nonsense oligonucleotide

<400> SEQUENCE: 8
ctcccactcg tcattcgac                                           19

<210> SEQ ID NO 9
<211> LENGTH: 10
<212> TYPE: PRT
<213> ORGANISM: Artificial Sequence
<220> FEATURE:
<223> OTHER INFORMATION: Cyclic decapeptide

<400> SEQUENCE: 9

Cys Ala Thr Asp Ile Lys Gly Ala Glu Cys
 1               5                  10

<210> SEQ ID NO 10
<211> LENGTH: 6
<212> TYPE: PRT
<213> ORGANISM: Artificial Sequence
<220> FEATURE:
<223> OTHER INFORMATION: Cyclic hexapeptide

<400> SEQUENCE: 10

Cys Lys Gly Ala Ile Cys
 1               5

<210> SEQ ID NO 11
<211> LENGTH: 4
<212> TYPE: PRT
<213> ORGANISM: Homo sapiens

<400> SEQUENCE: 11

Lys Gly Ala Ile
 1
```

METHODS OF INDUCING HAIR GROWTH AND COLORATION

RELATED APPLICATIONS

This application is a Continuation of PCT/US99/02362 filed Feb. 3, 1999, which is a Continuation-in-Part of U.S. Ser. No. 09/018,194 filed Feb. 4, 1998, which is a Continuation-in-Part of U.S. Ser. No. 08/93,683 filed Apr. 3, 1997 (abandoned), which is the U.S. National Phase of PCT/US95/10971 filed Aug. 30, 1995, which is a Continuation of U.S. Ser. No. 08/298,941, filed Aug. 31, 1994 (U.S. Pat. No. 6,103,689). The entire teachings of each of these applications are incorporated herein by reference.

BACKGROUND OF THE INVENTION

Normal hair follicles cycle between a growth stage (anagen), a degenerative stage (catagen), and a resting stage (telogen). The scalp hairs have a relatively long life cycle: the anagen stage ranges from two to five years, the catagen stage ranges from a few days to a few weeks, and the telogen stage is approximately three months (Fitzpatrick, T. B., et al., eds., DERMATOLOGY IN GENERAL MEDICINE (Vol. I), McGraw-Hill, Inc., 1993, pp. 290–291; Sperling, L. C., J. Amer. Acad. Dermatology (v. 25 No. 1, Part 1), pp. 1–17 (1991)). Shorter hairs found elsewhere on the body have corresponding shorter anagen duration. The morphology of the hair and the hair follicle changes dramatically over the course of the life cycle of the hair.

During anagen, the hair follicle is highly active metabolically (Sperling, L. C., J. Amer. Acad. Dermatology (v. 25, No. 1, Part 1), p.4 (1991)). The follicle comprises a follicular (dermal) papilla at the base of the follicle; epidermal matrix cells surrounding the follicular papilla and forming the base of a hair shaft; and the hair shaft that extends upwards from the papilla through the hair canal (Fitzpatrick, T. B., et al., eds., DERMATOLOGY IN GENERAL MEDICINE (Vol. I), McGraw-Hill, Inc., 1993). The matrix cells are the actively growing portion of the hair (Sperling, L. C., J. Amer. Acad. Dermatology (v. 25, No. 1, Part 1), p.6 (1991)). At catagen, the matrix cells retract from the papilla, and other degenerative changes occur (Sperling, L. C., J. Amer. Acad. Dermatology (v. 25, No. 1, Part 1), pp. 13–14 (1991)). A column of epithelial cells pushes the keratinized proximal shaft of the hair upwards (Sperling, L. C., J. Amer. Acad. Dermatology (v. 25, No. 1, Part 1), p. 3 (1991)), and cell death occurs within the follicle (Fitzpatrick, T. B., et al., eds., DERMATOLOGY IN GENERAL MEDICINE (Vol. I), McGraw-Hill, Inc., 1993, p. 291).

When the hair follicle reaches the telogen stage, the existing hair has a club-shaped proximal end, and a small bud (a remnant of the epithelial column that is found in catagen) at the base of the follicle (Sperling, L. C., J. Amer. Acad. Dermatology (v. 25, No. 1, Part 1), p. 3 (1991)). A telogen hair will not grow further (Fitzpatrick, T. B., et al., eds., DERMATOLOGY IN GENERAL MEDICINE (Vol. I), McGraw-Hill, Inc., 1993, p. 291).

The pigmentary system that colors hair involves melanocytes located in the matrix area of the follicle, above the follicular papilla (Fitzpatrick, T. B., et al., eds., DERMATOLOGY IN GENERAL MEDICINE (Vol. 1), McGraw-Hill, Inc., 1993, p. 292). Melanin pigments produced by the melanocytes flow along dendritic processes (Fitzpatrick, T. B., et al., eds., DERMATOLOGY IN GENERAL MEDICINE (Vol. I), McGraw-Hill, Inc., 1993, p. 292). The dendritic processes are phagocytized by the differentiating matrix cells that become part of the hair shaft; degradation of the phagocytosed material results in release of melanin granules into the cytoplasm (Fitzpatrick, T. B., et al., eds., DERMATOLOGY IN GENERAL MEDICINE (Vol. I), McGraw-Hill, Inc., 1993, p. 671), thus pigmenting the hair.

Alterations in normal hair pigmentation or growth may be caused by age, physiologic disease conditions, or injury especially, for example, exposure to ultraviolet-irradiation. The "graying" of hair, both normal (age-associated) or abnormal, is known as canities. Graying results from a progressive decrease in pigment present in the hair shaft, caused by loss of melanocytes (Fitzpatrick, T. B., et al., eds., DERMATOLOGY IN GENERAL MEDICINE (Vol. I), McGraw-Hill, Inc., 1993, p. 671; Gilchrest, B. A., SKIN AND AGING PROCESSES, CRC Press, 1984, p. 19). A decrease in the density of hair follicles is also associated with advancing age (Gilchrest, B. A., SKIN AND AGING PROCESSES, CRC Press, 1984, p. 20).

To date, the mechanism of melanocyte and keratinocyte injury, for example, from ultraviolet exposure or the aging process, has not been determined. Thus, little is known or available regarding a mechanism to manipulate the injury process to prevent cell death and thus prevent premature baldness or graying of hair or, conversely, to promote cell death and thus, unwanted hair growth.

SUMMARY OF THE INVENTION

The present invention is based on Applicants' discovery that basal layer epidermal melanocytes and keratinocytes undergo characteristic programmed cell death in response to injury. In particular, Applicants have shown that epidermal melanocytes and keratinocytes undergo programmed cell death, or apoptosis, and that apoptosis in these cells is mediated by the p75 nerve growth factor receptor/nerve growth factor pathway (p75 NGF-R/NGF), resulting in upregulation of Bcl-2 protein. As a result of Applicants' discovery, methods are herein provided to control or manipulate (e.g., induce or maintain or inhibit or eliminate) melanocyte and keratinocyte cell death by altering the effects of apoptosis. For example, apoptosis can be inhibited using methods described herein, resulting in hair growth and coloration. Conversely, apoptosis can be promoted by methods described herein, resulting in hair loss or depigmentation.

Keratinocytes and melanocytes of the basal layer of the epidermis express high affinity (trk e.g., trk A, trk C and trk E) and low affinity (p75) NGF receptors (p75 NGF-R, or $p75^{NTR}$). $p75^{NTR}$ is also referred to herein as the neurotrophin receptor and trk is referred to as the NGF-specific receptor. Neurotrophins (also referred to herein as neurotrophic factors) encompassed by the present invention include nerve growth factor (NFG), neurotrophin-3 (NT-3), neurotrophin-4/5 (NT4/5), brain-derived neurotrophic factor (BDNF) and other neurotrophic factors that share sequence identity and structural and functional similarity to the factors mentioned above. These factors all bind to p75 NGF-R. Also encompassed by the present invention are biologically active fragments of these factors, such as the 26 kD β-subunit of NGF. Biologically active fragments of the neurotrophins will bind to the p75 NGF-R. NGF, known to be produced by keratinocytes, protects cells from death when it binds to NGF receptors. In cells, this NGF effect is mediated in part by induction of the protective protein Bcl-2. Interestingly, basal epidermal keratinocytes and melanocytes express Bcl-2 protein. Specifically, as described herein, it has now been demonstrated that melanocytes expressing the p75 NGF-R can be rescued from apoptotic cell death by the occupation of the p75 NGF-R with NGF or a substance or pseudo-ligand capable of binding to the p75 NGF-R, which initiates the expression of the Bcl-2 protein. p75 contains a death domain motif and in cells that express p75, but not trk, NGF binding leads to cell death. When neurotrophins activate p75 together with receptors of the trk family, p75 evokes a survival signal. However, when p75 is activated alone, it may signal for apoptosis. As used herein, the term "activation of the receptor" means that when ligand binds to the receptor it results in initiating a pathway of cellular signaling.

Also as described herein, Applicants have now demonstrated that normal anagen hair follicles strongly express the p75 NGF-R and that p75 NGF-R expression is significantly reduced and limited to a few basal keratinocytes in telogen hair follicles.

As a result of these discoveries, methods are now available for inhibiting the process of apoptosis, or programmed cell death, in basal layer epidermal and follicular keratinocytes and melanocytes in vertebrates, specifically in humans. Thus, as a result of inhibition of apoptosis, the present invention relates to methods of inducing hair growth and coloration, and delaying hair loss and graying, as well as methods of inducing skin coloration in vertebrates. In addition, the present invention relates to methods of treating alopecia areata and baldness, as well as methods of preventing unwanted hair growth.

In one embodiment of the present invention, the invention relates to a method of preventing melanocyte and keratinocyte cell loss after injury by inhibiting apoptosis in epidermal and follicular melanocytes and keratinocytes. As described herein, Applicants have now demonstrated that p75 NGF-R mediated apoptosis is responsible for melanocyte loss after injury.

As described herein, Applicants demonstrate that $p75^{NTR}$ signals for cell apoptosis when activated alone, but instead signals for cell survival when activated together with receptors of the trk family. When p75 NGF-R is present alone, binding of NGF can induce apoptosis. The binding of ligand to p75 NGF-R, where the ligand can be, for example, a neurotrophin such as NGF, a biologically active fragment of a neurotrophin, (e.g., the 26 kD β-subunit of NGF) or pseudo-ligand (also referred to herein as a neurotrophin analog, or NGF analog) such as a peptide or cyclic peptide (wherein the peptide contains the sequence lysine-glycine-lysine, or lysine-glycine-alanine, in suitable three dimensional configuration for binding to p75) can inhibit the p75 NGF-R induced apoptotic pathway of cell death, resulting in the continued growth/proliferation, pigment production and pigment transfer to keratinocyte by epidermal melanocytes. Alternatively, epidermal melanocyte and keratinocyte cell loss can be prevented by upregulating the expression of Bcl-2 and other related anti-apoptotic proteins of the Bcl-2 family. Alternatively, cell loss can be prevented by down-regulating the expression of the p75 NGF-R in the melanocytes and keratinocytes. Increasing the ratio of $p75^{NTR}$ to trk A expression can shift the effect of NGF from one of enhancing cell survival to one of promoting apoptotic cell death in melanocytes. As further described herein, Applicants demonstrate that the apoptotic signaling pathways following activation of the $p75^{NTR}$ involve sphingomyelin turnover and ceramide generation by inducing transcription of c-jun mRNA, stimulating JNK, activating caspase-3 and inducing characteristic DNA fragmentation. Signaling through the p75 receptor requires receptor aggregation, and inhibiting receptor aggregation inhibits apoptosis.

In another embodiment of the invention, the invention relates to a method of inducing hair growth in a vertebrate by upregulation of the expression of the p75 NGF-R on keratinocytes in a vertebrate, such as humans, by introducing into epidermal keratinocytes a nucleotide sequence encoding the p75 NGF-R. The p75 NGF-R gene product is expressed on the surface of the keratinocytes, and becomes available to bind to its naturally occurring ligand, NGF, or to another substance that mimics the binding activity of NGF (i.e., a pseudo-ligand). The p75 NGF-R binds its ligand, or pseudo-ligand, resulting in the expression of the protein, Bcl-2 and/or other related Bcl-2 family proteins, which protects the keratinocyte from apoptosis.

Alternatively, the upregulation of the expression of the p75 NGF-R can be accomplished by introducing into the keratinocyte a substance, such as a transcription activator protein, which initiates the transcription of the p75 NGF-R gene. It is important to remember that it is the ratio of p75 to trk that determines which signaling pathway will be activated by the neurotrophic ligand. Raising p75 level alone may enhance cell survival if the p75/trk ratio is too low.

In another embodiment of the present invention, inhibiting apoptosis in keratinocytes found in hair follicles can inhibit premature entry into catagen (hair follicle regression). Hair growth can be induced or prolonged when the keratinocyte p75 NGF-R is occupied by ligand, such as NGF, or pseudo-ligand such as a peptide or cyclic peptide containing the sequence lysine-glycine-lysine or lysine-glycine-alanine in proper conformation, which inhibits the p75 NGF-R induced apoptotic pathway of cell death, and results in the continued growth/proliferation of hair. Hair growth can also be induced or prolonged by the upregulation of the expression of the Bcl-2, and/or related proteins, protein in the keratinocytes, either by the introduction of a nucleotide sequence encoding the Bcl-2 protein or the Bcl-2 related proteins, or by the introduction of a substance that initiates transcription of the gene encoding the Bcl-2 protein, or the related protein.

In another embodiment of the present invention, the invention relates to a method of inducing hair color in a vertebrate, such as a human, by inhibiting p75 NGF-R mediated apoptosis of epidermal melanocytes.

In another embodiment of the present invention, the invention relates to a method of inducing skin color in a vertebrate, particularly a human, by inhibiting p75 NGF-R mediated apoptosis of epidermal melanocytes. As described above, Applicants have shown that peptides containing the sequence lysine-glycine-alanine (KGA) in proper conformation (e.g., a β-loop conformation) specifically bind p75 NGF-R and inhibit p75 NGF-R mediated apoptosis of melanocytes.

Conversely, apoptosis can be promoted in melanocytes and keratinocytes in humans, resulting in cell death. For example, cell death may be desirable to prevent unwanted hair growth (e.g., on women's faces or forearms). This can be accomplished, for example, by blocking nerve growth factor from binding to p75 NGF-R, thereby decreasing, or completely inhibiting production of Bcl-2 protein or by promoting the activation of the $p75^{NTR}$ in the absence of activating trk receptors. Thus, apoptotic cell death would be promoted.

Another embodiment of the present invention relates to a method of identifying a substance capable of inhibiting apoptosis in melanocytes or keratinocytes by determining the effect the substance has on the activation of p75 nerve growth factor receptor.

Alternatively, the method of identifying a substance capable of inhibiting apoptosis in melanocytes or keratinocytes can be accomplished by determining the effect the substance has on Bcl-2 protein expression.

Thus, as a result of Applicants' discovery of the role of p75 NGF-R induced apoptosis in epidermal and follicular melanocytes and keratinocytes, methods are now available to inhibit apoptotic cell death in epidermal and follicular melanocytes and keratinocytes, including methods of inducing or prolonging hair growth, hair coloration and skin coloration and methods of decreasing hair growth, hair coloration and skin coloration.

BRIEF DESCRIPTION OF THE FIGURES

FIG. 1A is a photomicrograph depicting the effect of UV irradiation with 10 mJ/cm$^2$ on melanocytes.

FIG. 1B is a photomicrograph depicting the effect of sham irradiation on melanocytes.

FIG. 1C is a photomicrograph depicting the effect of UV irradiation with 10 mJ/cm$^2$ on MM4 cells.

FIG. 1D is a photomicrograph depicting the effect of sham irradiation on MM4 cells.

FIG. 1E is a photograph of an agarose gel stained with ethidium bromide depicting the effect of UV irradiation, of MM4 cells on DNA fragmentation.

FIG. 1F is a photomicrograph depicting the effect of UV irradiation of melanocytes on fragmentation of nuclear chromatin.

FIG. 1G is a photomicrograph depicting the effect of UV irradiation of melanocytes on homogenization of nuclear chromatin.

FIG. 1H is a bar graph depicting the percentage of propidium iodide-positive melanocytes after sham irradiation, UV irradiation with 10 mJ/cm$^2$ or UV irradiation with 25 mJ/cm$^2$.

FIG. 2F is a photomicrograph depicting melanocyte cell morphology after UV irradiation daily for three days with 10 mJ/cm$^2$ and supplemented with diluent alone.

FIG. 2G is a photomicrograph depicting MM4 cell morphology after UV irradiation once with 10 mJ/cm$^2$ and supplemented with diluent alone.

FIG. 2H is a photomicrograph depicting melanocyte cell morphology after UV irradiation daily for three days with 10 mJ/cm$^2$ and supplemented with 50 ng/ml NGF.

FIG. 2I is a photomicrograph depicting MM4 cell morphology after UV irradiation once with 10 mJ/Cm$^2$ and supplemented with 50 ng/ml NGF.

FIG. 4A is a graphic representation depicting the effect of NGF on Bcl-2 expression in MM4 cells UV-irradiated with 10 mJ/cm$^2$.

FIG. 4B is a graphic representation depicting the effect of NGF on Bcl-2 expression in MM4 cells sham irradiated.

FIG. 4C is a photograph of a Western blot depicting the effect of NGF on Bcl-2 expression in MM4 cells UV-irradiated or sham irradiated.

DETAILED DESCRIPTION OF THE INVENTION

Figure 2A:
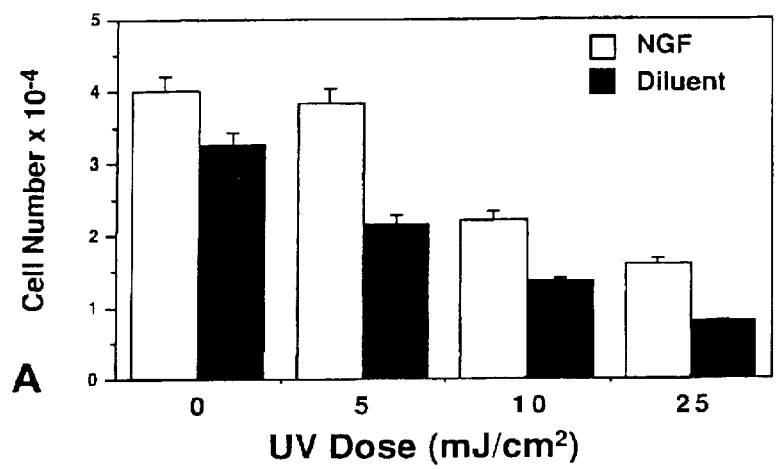
FIG. 2A is bar graph depicting cell yields of melanocytes after 3 daily UV irradiations of 0, 5, 10 and 25 mJ/cm$^2$.

The present invention is based on Applicants' finding that basal layer melanocytes and keratinocytes undergo programmed cell death, or apoptosis. Specifically, Applicants have demonstrated that melanocytes and keratinocytes of the basal layer of the epidermis and the hair follicle undergo apoptosis. Apoptosis is an active process of self-destruction that occurs in vertebrate cells. Apoptosis follows a distinct pattern of events characterized by plasma membrane blebbing, cell volume contraction, nuclear pyknosis and inter nucleosomal DNA degradation following the activation of $Ca^+/Mg^{2+}$ dependent endonucleases. (Hockenberry, D. M., et al., Cell 75:241–251 (1993); Garcia, I., et al., Science 258:302–304 (1992)). Apoptosis is a highly conserved mechanism among species. Cells carry in their nuclei a genetic program for apoptosis, that can be activated upon the proper triggering, such as in response to changes in levels of hormones or growth factors in the cellular environment. (Allsopp, T. E., et al., Cell 295–307 (1993); Barinaga, M. et al., Science 259:762–763 (1992); Barinaga, M., et al., Science 263:754–755 (1994)). The "apoptotic" genes encode proteins which will induce apoptosis. However, recent evidence suggests that cells that do not undergo apoptosis express protective proteins, one of which is Bcl-2, which interact with the apoptotic proteins, sequester them and prevent their activity (Allsopp, T. E., et al., Cell 295–307 (1993)). It thus appears that a mechanism exists to protect cells from apoptosis.

To examine if UV-induced melanocyte death is apoptotic, cultures of pure human epidermal melanocytes or the human melanoma cell line MM4 (provided by Dr. U. Stierner, Goteborg, Sweden) were exposed to 5, 10 or 25 $mJ/cm^2$ UV irradiation, doses well within the physiologic UV range that reaches the basal layer of the epidermis during casual sun exposure. (See Example 1). Sham irradiated control cultures were handled identically but placed under a dark cloth adjacent to the UV beam. After 1–3 daily irradiations, many cells were detaching from the dish surface (See FIGS. 1A and 1C), while the majority of the cells in sham irradiated control cultures appeared healthy (See FIGS. 1B and 1D).

Total cellular DNA isolated from paired UV-irradiated cultures displayed the characteristic endonuclease-induced DNA fragmentation into multimers, the so-called DNA ladder, while DNA of sham irradiated controls was not fragmented (FIG. 1E). Duplicate UV-irradiated cultures stained with propidium iodide displayed the characteristic compaction margination and fragmentation of nuclear chromatin, as well as homogenous nuclear staining (FIGS. 1F and 1G). In sham irradiated cultures, fewer than 6% of the cells stained positively with propidium iodide. In contrast, approximately 30% and 60% of cells irradiated with 10 and 25 $mJ/cm^2$ respectively were propidium iodide positive (FIG. 1H). These data strongly suggest that UV irradiation induces apoptotic death in cells of melanocytic origin.

However, melanocytes in vivo are not known to undergo apoptosis after UV-irradiation. As described herein, Applicants have demonstrated that these cells have a mechanism necessary to protect them from apoptotic cell death.

It had previously been shown that both the high affinity and low affinity nerve growth factor receptors, 140 kD and trkA and p75 NGF-R, were expressed in vitro on the surface of appropriately stimulated human melanocytes. (Peacocke, M., et al., Proc. Natl. Acad. Sci. U.S.A. 85:5282–5286 (1988); Yaar, M., et al., Clin. Res. 40:531A (1992)). It had also been shown that keratinocytes express nerve growth factor. (Yaar, M., et al., J. Cell Biol. 115:821–828 (1991); DiMarco, E., et al., J. Biol. Chem. 266:21718–21722 (1991)).

Applicants now describe herein, that nerve growth factor enhances the survival of human melanocytes after injury, for example, due to ultraviolet light exposure or growth factor deprivation.

Cultured human melanocytes were exposed to a solar simulator (5, 10, 25 $mJ/cm^2$ UVB dose) or sham irradiated as described in Example 1 and then maintained in suboptimal serum-free medium, and continuously provided with either 50 ng/ml nerve growth factor or diluent alone. (See Example 2). After UV irradiation, the majority of melanocytes and MM4 cells not supplemented with NGF were detaching from the dish surface. (See FIGS. 2F and 2G). In contrast, cultures supplemented with NGF appeared healthy. (See FIGS. 2H and 2I).

Cell yields of melanocytes (FIG. 2A) and MM4 cells (FIGS. 2B and 2C) irradiated with 10 $mJ/cm^2$ and supplemented with 50 ng/ml NGF were significantly higher than those of cells supplemented with diluent alone (melanocytes: 7 experiments $p<0.0085$; MM4 cells: 4 experiments $p<0.0001$, ANOVA). Furthermore, supplementation with basic fibroblast growth factor (bFGF), a major mitogen for cells of melanocytic origin (Halaban, R., et al., In Vitro Cell Devel. Biol. 23:47–52 (1987); Halaban, R., et al., J. Cell Biol. 107:1611–1619 (1988)), failed to improve MM4 cell survival after UV irradiation despite its mitogenic effect on sham irradiated cells (FIGS. 2D and 2E).

To explore the mechanism of the striking response of UV irradiated cells to NGF, paired cultures were irradiated with UVB light (5, 10 or 25 $mJ/cm^2$ UVB dose), or sham irradiated, and then incubated with antibodies to the high affinity component of the NGF receptor, trk. Melanocytes in UV-treated cultures displayed more trk receptors than sham irradiated controls. Northern blot analysis checking the mRNA levels of the p75 NGF-R showed several-fold higher transcript levels in NGF-supplemented melanocytes than in diluent controls.

To determine if melanocytes undergo p75 NGF-R mediated apoptotic cell death after UV irradiation, melanocytes were exposed to UVB (10 or 25 $mJ/cm^2$) or were sham irradiated, as described in Example 1, then maintained in suboptimal serum-free medium. Both UVB irradiation and suboptimal culture conditions, previously shown to induce p75 NGF-R expression on melanocytes, induced the DNA fragmentation patterns classic for apoptosis.

Figure 3A:
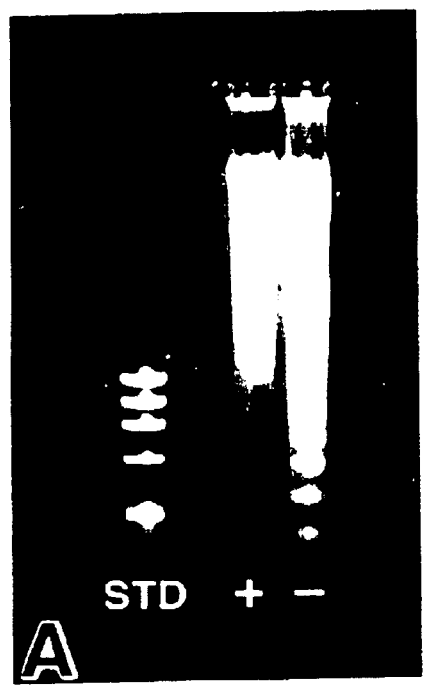
FIG. 3A is a photograph of an agarose gel stained with ethidium bromide depicting the effect of UV irradiation of MM4 cells supplemented with NGF on DNA fragmentation.
Figure 3B:
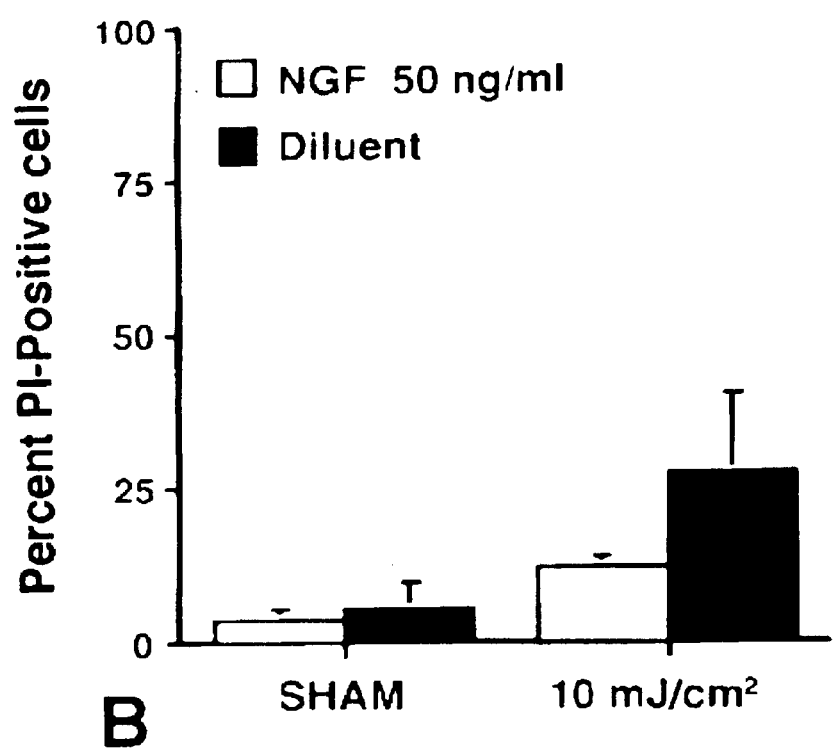
FIG. 3B is a bar graph depicting the percentage of propidium iodide-positive melanocytes after sham irradiation or UV irradiation with 10 mJ/cm and then treatment with 50 ng/ml NGF or diluent alone.

To determine whether NGF can rescue injured melanocytes from apoptosis, duplicate cultures were irradiated as described above, and maintained in medium containing 50 ng/ml NGF or diluent alone. Irradiated cultures not supplemented with NGF showed the characteristic DNA fragmentation, while cultures supplemented with NGF showed far less fragmentation (FIG. 3A). As described in Example 3, within twenty-four hours, in NGF-treated versus control melanocytes, 12% versus 30% of nuclei showed fragmentation (p less than 0.05, paired test). (FIG. 3B). Cell yields and thymidine labeling index determined daily for 19 days were higher in NGF-treated cultures (p less than 0.001), up to 6.5-fold and 10-fold, respectively.

To determine if melanocyte apoptosis is mediated by p75 NGF-R, cultures were treated as above, and then incubated in the presence of a blocking anti-human p75 NGF-R monoclonal antibody believed to act as a pseudo-ligand for the p75 NGF-R. (Anti-human p75 NGF-R monoclonal antibody courtesy of Moses V. Chao, Cornell University Medical Center, New York, N.Y.; Ross, et al., Proc. Natl. Acad. Sci. 81:6681 (1984)). Like NGF, the antibody suppressed melanocyte apoptosis in UV-irradiated cultures, while anti-rat p75 NGF-R antibody that did not bind the human p75 NGF-R had no effect.

Northern blot analysis of melanocyte RNA from donors of different ages showed that p75 NGF-R was higher in older donors, while in contrast the level for other growth factor receptors was unchanged or decreased with age, suggesting a greater vulnerability to apoptosis with aging, consistent with the clinical tendency for older persons to experience progressive hair loss.

Thus, one embodiment of the present invention relates to a method of preventing or inhibiting melanocyte cell loss after injury. The melanocytes are located in the basal epidermal layer and include melanocytes located in the skin and in hair follicles. The type of injury includes injury due to exposure to ultraviolet light, especially UVB, for example, in habitually sun-exposed skin, and injury due to the normal aging process. Injuries can also include disease conditions such as alopecia areata, telogen effluvium, and androgenic alopecia. The treatment of male-pattern baldness is also encompassed by the present invention.

More specifically, the invention relates to methods of preventing, or inhibiting, apoptosis in melanocytes and keratinocytes. As described above, Applicants have shown that apoptosis in melanocytes is mediated by the p75 NGF receptor. If the receptor is occupied, that is, if the receptor has bound an appropriate ligand, apoptosis is inhibited in the cell. Examples of appropriate ligands include neurotrophins, nerve growth factor, biologically active fragements of neurotrophins and NGF, such as the NGF 26 kD β-subunit, and peptides or other small molecules that mimic the region of neurotrophins and NGF that bind to the $p75^{NTR}$, also referred to herein as p75 psuedo-ligands. Such pseudoligands small peptides such as the cyclic peptide, CATDIK-GAEC (SEQ ID NO:9) described herein. The psuedo-ligands of the present invention bind to the $p75^{NTR}$ but do not induce p75 receptor aggregation, thus do not induce apoptotic pathway signaling in the cell.

An example of an inappropriate ligand is aggregated Alzheimer's disease associated protein, β-amyloid. Binding of β-amyloid to the $p75^{NTR}$ activates the receptor and results in apoptotic cell death of the melanocytes mediated by JNK activation.

Applicants demonstrate herein that supplementation of normal human melanocytes with β-amyloid 1–40 peptide at low concentrations ($\leq 1$ microM) leads to extensive outgrowth of dendrites, the melanocyte cell processes analogous to neurites of neurons, without decreasing cell yields. At higher concentrations of β-amyloid peptide, melanocyte cell yields decrease progressively and the remaining cells appear unhealthy. Additionally, in these cultures there is focal development of plaque-like structures consisting of aggregated dying melanocytes, similar to the in vivo "senile plaques" observed in patients with AD.

Applicants further demonstrate herein that maintaining melanocytic cell cultures in $\geq 25$ microM beta-amyloid 1–40, compared to control cultures, significantly increases the proportion of apoptotic cells and upregulates Bax protein expression approximately three fold. Recent in vivo and in vitro data suggest that the beta-amyloid induced-neuronal death exhibits classical characteristics of programmed cell death or apoptosis (Cotman, C. W. and Anderson, A. J., Mol. Neurobiol., 10:19–45 (1995); Su, J. H., et al., Neuroreport, 5:2529–2533 (1994)). The molecular pathways that regulate apoptosis in neurons have been identified in part. Evidence suggests that the product of the proto-oncogene Bcl-2 delays the onset of apoptosis in neurons that are dependent for survival on neurotrophic factors (Allsopp, T. E., et al., Cell, 73:295–307 (1993); Garcia, I., et al., Science, 258:302–304 (1992). Conversely, over expression of a 21 kD Bcl-2-associated protein, Bax, accelerates apoptotic death of cells (Oltvai, Z. N, et al., Cell, 74:609–619 (1993)).

Melanocytes express both the low affinity $p75^{NTR}$ and high affinity 140 kD trk A ($p140^{trkA}$) receptors for NGF and providing NGF to melanocytes results in activation of the $p140^{trkA}$ pathway, presumably through co-ordinate binding of $p140^{trkA}$ and multiple $p75^{NTR}$ molecules as postulated to occur in neurons exposed to NGF, that in turn activates an intracellular signal transduction pathway leading to enhanced expression of Bcl-2 and enhanced cell survival.

Applicants further demonstrate herein that beta-amyloid binds competitively to the $p75^{NTR}$. Studies previously published suggest that the specific binding site for the $p75^{NTR}$ is amino acids 29–36 of the resulting NGF protein (Ulrich, A., et al., Nature 303:821–825 (1983), and that if the sequence lysine-glycine-lysine (residues 32–34 of NGF) is changed to lysine-glycine-alanine, the peptide has approximately half the affinity for the receptor as native NGF. Amino acid residues 28–30 of the beta-amyloid protein are lysine-glycine-alanine. Furthermore, computerized structure analysis of beta-amyloid reveals that these amino acids have a high probability of being in a loop turn of the protein, suggesting a high probability that this beta-amyloid peptide sequence plays a role in receptor binding.

A cyclic decapeptide was therefore synthesized by attaching two cysteine residues to the beginning and the end of the -amyloid fragment consisting of amino acids 24–31: VGSNKGAI (SEQ ID NO: 1). Cold peptide competitively inhibited $^{125}$I-beta-amyloid binding, with 50% inhibition occurring at 25 nM. Furthermore, beta-amyloid 200 nM reduced by cell yields by about 60% (p<0.02), but this cell loss was blocked by the peptide (200 nM). Peptide alone had no effect on cell yield. These findings indicate that apoptosis of neurons in Alzheimer's Disease results from the interaction of beta-amyloid with $p75^{NTR}$. The data also suggest that beta-amyloid-mediated death of neurons may be prevented by delivery of a synthetic peptide that blocks the beta-amyloid binding sites.

Binding of NGF to $p75^{NTR}$ is mediated through amino acid residues 29–36, TDIKGKEV (SEQ ID NO: 2), that are part of the beta-hairpin loop of NGF (Ibánez, C. F., et al., Cell, 69:329–341 (1992)). If lysine (K) at position 34 is replaced by alanine (A), the resulting mutant NGF molecule still binds $p75^{NTR}$ but with 50% lower affinity. Interestingly, in beta-amyloid the amino acid residues 28–30, which are present in both the 1–40 and the 25–35 beta-amyloid peptides, are KGA, a sequence that appears to permit $p75^{NTR}$ binding by beta-amyloid. Computerized structure analysis of beta-amyloid suggests that the KGA residues have a high probability (>60%) of being in a loop turn, the highest probability of any portion of this 40 amino acid peptide, suggesting that this sequence constitutes a binding site for $p75^{NTR}$. Furthermore it was reported that expression of $p75^{NTR}$ enhances the toxic effect of beta-amyloid on cells, possibly through binding and activation of the receptor.

Based on the above data, it is reasonable to believe that the specific three amino acid sequence lysine-glycine-alanine (KGA) in the beta-amyloid protein binds the 75 kD transmembrane neurotrophin receptor on CNS neurons, activating the programmed cell death pathway, mediated in part by an increase in intracellular Bax levels.

It is also reasonable to believe that competitively inhibiting the binding of beta-amyloid peptide blocks this aberrant receptor activation and the resulting apoptosis. For example, providing full-length NGF, or a biologically active fragment, analog, derivative, variant or mutant thereof results instead in preferential binding of $p75^{NTR}$ coordinately with $p140^{trkA}$ binding, leading to activation of a second signal transduction pathway that results in neuronal cell survival.

The term "biological activity" of NGF, or a fragment, derivative, analog, variant or mutant NGF, is defined herein as the activity of the NGF to specifically bind to the $p75^{NGF}$ receptor. For example, an NGF mimic, or psuedo-ligand can comprise the amino acid sequence KGK or KGA, and the sequence can be in suitable three-dimensional conformation to bind to p75. Such activity can be measured by the methods described herein, or by other methods known to those skilled in the art. Another biological activity of an NGF fragment, analog, derivative, variant or mutant is the antigenic property of inducing a specific immunological response as determined using well-known laboratory techniques. For example, a biologically active NGF fragment can induce an immunological response which produces antibodies specific for the NGF (anti-NGF antibodies).

Mammalian NGF is a protein, consisting of three subunits $\alpha$, $\beta$, and $\gamma$, which interact to form an approximately 130 kD complex. (Ulrich, A., et al., Nature 303:821–825 (1983)). However, all known effects of NGF are mediated by the 26 kD beta-subunit through its receptor. There are two types of NGF receptors, one of a low molecular weight of approximately 75 kD, and the other of a higher molecular weight of approximately 140 kD. Both are believed necessary for the high affinity binding of NGF which is necessary for cellular response. The higher molecular weight receptor was recently found to be the protooncogene, trk, which is a member of the tyrosine kinase family. (Yaar, M., et al., J. Cell Biol., 115:821–828 (1991); Chao, M., et al., *Science* 232:518–521 (1986); Klein, R. S., et al., Cell 65:189–197 (1991)). NGF has been sequenced and cloned as described in Ulrich, A., et al., Nature, 303:821–825 (1983), the teachings of which are herein incorporated by reference. Thus, the entire NGF protein complex, one of its active subunits, such as the 26 kD subunit, or any biologically active fragment of NGF can be used to occupy the receptor. The biological activity of an NGF protein fragment can be determined by in vitro bioassay, for example, as described in DiMarco, E., et al., J. Biol. Chem., 266:21718–21722 (1991), the teachings of which are herein incorporated by reference.

Other substances that mimic NGF can act as a pseudo-ligand for the receptor. For example, the anti-human p75 NGF-R antibody described in Ross, et al., Proc. Natl. Acad. Sci. 81:6681 (1984) binds to p75 NGF-R and suppresses apoptosis in melanocytes. Other pseudo-ligands are KGA-containing peptides that bind $p75^{NTF}$. Examples of such pseudo-ligands are the cyclic KGA-containing hexapeptides and decapeptides described, for example, in SEQ ID NOs.4, 9 and 10. These substances include other neurotrophic factors and neurotrophins, such as NT-3, -4, and -5, with structural and functional similarity to NGF and are also capable of binding to the p75 NGF-R. (DiMarco, E., et al., J. Biol. Chem., 268:24290–24295 (1993); Yaar, M., et al., J. Invest. Derm., 100:554 (1993)). Additional substances, either protein or chemical in nature, can be produced and evaluated for their NGF-R binding ability. For example, a chemical substance can be produced that mimics the composition of NGF. This substance can be evaluated as described above for NGF activity.

Alternatively, a method of preventing epidermal melanocyte cell loss can encompass downregulating the expression of the p75 NGF-R on epidermal melanocytes. This would also result in fewer unoccupied receptor molecules and hence, suppress apoptosis and prevent melanocyte cell loss. Downregulation can be accomplished, for example, by introducing into the melanocyte a substance that inhibits or decreases the transcription of the gene encoding the p75 NGF-R. For example, an antisense oligonucleotide which is complementary to the cellular mRNA encoding the p75 NGF-R can be introduced into the melanocyte in such a manner that the antisense oligonucleotide hybridizes with the mRNA, thereby preventing translation of the mRNA into p75 NGF-R protein.

Alternatively, epidermal melanocytes can be contacted with a substance which binds to p75 nerve growth factor receptor expressed on the surface of the melanocytes. The substance, for example, can be nerve growth factor in a pharmaceutically acceptable carrier or an antibody capable of binding to p75 nerve growth factor and acting as a pseudo-ligand. Pseudo-ligands include substances that mimic nerve growth factor, such as, e.g., peptides, the KGK and KGA containing peptides described herein, organic molecules, antibodies and antibody fragments.

Pseudo-ligand antibodies which can be used in the present invention are capable of binding to p75 nerve growth factor receptor. The term antibody is intended to encompass both polyclonal and monoclonal antibodies. The preferred pseudo-ligand antibody is a monoclonal antibody reactive with a p75 nerve growth factor receptor. The term antibody is also intended to encompass mixtures of more than one antibody reactive with a p75 nerve growth factor receptor (e.g., a cocktail of different types of monoclonal antibodies reactive with a p75 nerve growth factor receptor). The term antibody is further intended to encompass whole antibodies, biologically functional fragments thereof, and chimeric antibodies comprising portions from more than one species, bifunctional antibodies, etc. Biologically functional antibody fragments which can be used are those fragments sufficient for binding of the antibody fragment to the p75 nerve growth factor receptor to occur.

The chimeric antibodies can comprise portions derived from two different species (e.g., human constant region and murine variable or binding region). The portions derived from two different species can be joined together chemically by conventional techniques or can be prepared as single contiguous proteins using genetic engineering techniques. The portions derived from two different species can also be produced by recombinant means and then joined as described above. DNA encoding the proteins of both the light chain and heavy chain portions of the chimeric antibody can be expressed as contiguous proteins or can be produced by recombinant means and joined using techniques known to those of skill in the art.

One mechanism by which p75 induces apoptosis may involve the cellular ratio of $p75^{NTR}$ to TRK in combination with the level of NGF. The abundance of NGF, the (A neurotrophin that presumptively enhances the survival of cells that express both of its receptors, decreases with age (Larkfors, L. et al. Brain Res. 1987; 427:55–60). In addition, the Applicants have found a prominent increase in the expression of the apoptotic $p75^{NTR}$ with aging (Yaar, M. et al., J. Invest Deratol., 1997;108:568). These data suggest that a relative lack of NGF and/or increased levels of an apoptosis-inducing ligand such as beta-amyloid may lead to apoptotic loss of cells. Furthermore, as described herein ligand binding to the $p75^{NTR}$ resulted in receptor aggregation, which led to the initiation of the apoptotic pathway. Psuedo-ligands that bind to the $p75^{NTR}$ but do not aggregate the receptor, such as the cyclic peptide CATDIK-GAEC (SEQ ID NO:9), can inhibit apoptosis.

The end result of p75 NGF-R and trk binding to its ligand is the expression of the protective protein, Bcl-2. Bcl-2 has been shown to prevent some classes of cell death in lymphocytes and neurons. (Veis, D. J., et a., Cell 75:229–240 (1993)). As described in Example 4, Applicants have now shown the expression of Bcl-2 by injured melanocytes after treatment with NGF. Apoptosis can be inhibited by the expression of the protective protein, Bcl-2. Thus, another method of preventing melanocyte cell loss comprises a method of upregulating expression of the Bcl-2 protein in melanocytes. This can be accomplished, for example, by inserting a nucleotide sequence encoding Bcl-2 into an expression vector capable of expressing the encoded Bcl-2 in vertebrate cells. Such an expression vector can be constructed, for example, as described in Allsopp, T. E., et al., Cell 73:295–307 (1993), the teachings of which are herein incorporated by reference. This Bcl-2 expression vector can then be introduced into melanocytes using standard laboratory techniques, such as, for example, microinjection, calcium-phosphate precipitation, or microprojectible bombardment.

Alopecia areata (AA) is a common disease of the hair follicle, affecting about 2% of new patients attending dermatology clinics in the United States and in Britain (Price, V. H., J. Invest. Dermatol., 96:685 (1991)). In alopecia areata, the hair follicle, in response to some unknown signal or injury, is suddenly precipitated into premature telogen, and then cycles in a shortened aborted cycle in which it is repeatedly arrested part way through early anagen. The follicle may remain in this arrested state but is capable of resuming normal growth after months or years. The nature of the signal or injury and the anatomical target for this abnormality are unknown.

Histologically, AA is characterized by peribulbar lymphocytic infiltrate of predominantly T helper cells (Lever, W. F. and Schaumburg-Lever, G., eds., HISTOPATHOLOGY OF THE SKIN, J.B. Lippincott Co., Philadelphia, Pa., 1990, pp. 223–224), strongly suggesting the involvement of the cellular immune system perhaps through a loss of discrimination of self and non-self antigens (Goldsmith, L. A., J. Invest. Dermatol., 96:985–1005 (1991)). Alternatively, an intrinsic abnormality in the follicular keratinocyte could be activated under the influence of internal or external triggers which eventually may lead to cellular degeneration and peribulbar inflammatory infiltrate. However, to date no specific antigen has been identified to support the autoimmune theory and no specific intrinsic difference has been reported between normal bulbar and AA keratinocytes.

Figure 5A:
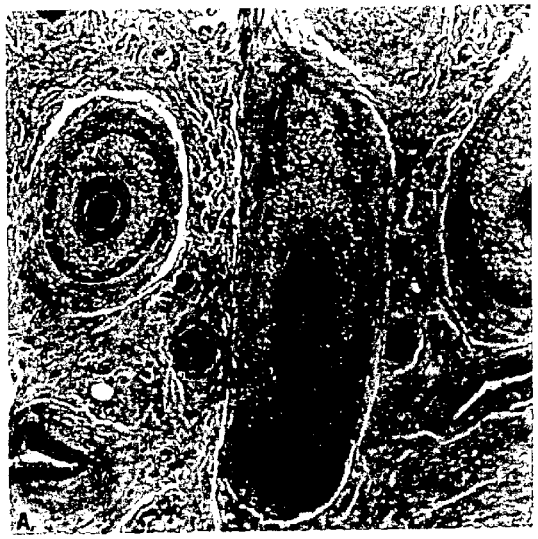
FIGS. 5A and 5B are photomicrographs showing the high levels of p75 NGF-R expression in melanocytes and bulbar keratinocytes of the outer root sheath in the lower portion of anagen hairs.
Figure 5B:
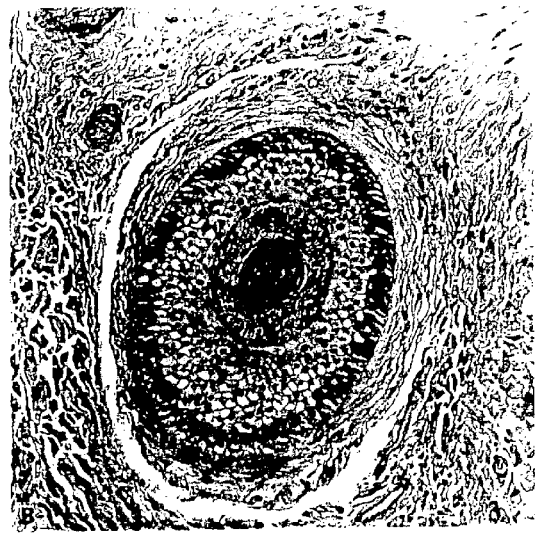
Figure 5C:
FIG. 5C is a photomicrograph showing p75 NGF-R levels in melanocytes and keratinocytes of telogen hairs.

As described in Example 5, indirect immunofluorescent studies were performed on biopsy material obtained from normal subjects and alopecia areata patients in an effort to detect differences in the NGF signaling system during conditions characterized by keratinocyte and melanocyte death. Results show high levels of p75 NGF-R in melanocytes and bulbar keratinocytes of the outer root sheath in the lower portion of anagen hairs (FIGS. 5A and 5B), suggesting a role for p75 NGF-R in hair growth. p75 NGF-R levels were significantly reduced or p75 NGF-R was absent melanocytes and keratinocytes of telogen hairs (FIG. 5C). Furthermore, in melanocytes and keratinocytes in anagen hairs of AA patients, significantly lower levels of p75 NGF-R was also detected (FIGS. 5D and 5E), indicating that decreased levels of this receptor may be involved in the pathogenesis of AA by precipitating anagen hairs into early telogen.

These findings strongly suggest that loss of the p75 NGF-R may lead to bulbar keratinocyte apoptosis and shift the hair follicle towards telogen. Decreased p75 NGF-R in anagen hair of AA patients may be the initial insult which triggers telogen effluvium in these patients.

Thus, in another embodiment of the present invention, the invention relates to a method of inducing hair growth, or maintaining hair growth in a vertebrate such as a human, by inhibiting apoptosis in keratinocytes. This is especially useful to delay or prevent hair loss in humans, for example, in male pattern baldness. Hair growth is induced by maintaining hairs in the anagen phase, and preventing the initiation of the telogen phase. As described above, p75 NGF-R levels were significantly reduced, or absent in alopecia areata patients. Thus, it is reasonable to believe that if the level of NGF-R expression on the surface of hair follicle keratinocytes is increased in the p75/trk ration is too low, the hairs are maintained in the anagen phase resulting in hair growth. Upregulating the expression of the p75 NGF-R can be accomplished by inserting a nucleotide sequence encoding the p75 NGF-R into an expression vector capable of expressing the encoded receptor protein in a vertebrate cell and introducing the receptor vector into the keratinocyte, resulting in expression of the encoded receptor. p75 NGF-R expression vectors can be constructed as described in, e.g., Rabizadeh, S., et al., Science 261:345–348 (1993); Morgenstern, J. P., et al., Nucleic Acids Res. 18:3587 (1990). This p75 NGF-R expression vector can be introduced into keratinocytes using standard laboratory techniques, such as, for example, microinjection, calcium-phosphate precipitation, or microprojectile bombardment. The cDNA sequences for human, rat and chicken p75 NGF-R are known. (Johnson, D., et al., Cell 47:545–554 (1986); Radeke, M. et al., Nature 325:593–597 (1987) and Large, T. H., et al., Neuron 2:1123–1134(1989); Huer, J. G., et al., Devl. Biol. 137:287–304 (1990), respectively, the teachings of which are incorporated by reference).

Alternatively, a substance can be introduced into epidermal keratinocytes that upregulates the expression of the p75 NGF-R, such as a transcription factor that promotes the transcription of the gene encoding the p75 NGF-R.

Based on the data presented herein, Applicants reasonably expect that p75 NGF-R/NGF mediated apoptosis also occurs in epidermal keratinocytes. Thus, the binding of p75 NGF-R and trk to ligand in epidermal keratinocytes results in the expression of the anti-apoptotic protein, Bcl-2. As described herein, p75 antagonistic cyclic peptides in a concentration of 0.01–100 micromolar significantly retard catagen development.

Another method of inducing hair growth encompassed by the present invention relates to upregulating the expression of Bcl-2 in epidermal keratinocytes. Upregulation of Bcl-2 expression can be accomplished by expressing the encoded Bcl-2 protein in keratinocytes in a similar manner as the expression of Bcl-2 protein in melanocytes as discussed above.

As discussed above, in biopsies from patients with AA, p75 NGF-R expression in keratinocytes of anagen hairs is significantly reduced or totally absent. In AA, the p75 NGF-R can be bound in vivo by a pathogenic autoantibody that precludes further binding of commercial antibodies. To pursue the possibility that reduced levels of p75 NGF-R in AA are the result of a bound autoantibody, direct immunofluorescent studies can be performed on cross section from AA patients to determine if human immunoglobulins are bound in areas known to express p75 NGF-R.

Another embodiment of the present invention relates to methods of inducing, or maintaining, hair coloration in a vertebrate comprising inhibiting apoptosis in epidermal melanocytes. Epidermal melanocytes produce melanin pigment in organelles called melanosomes and transfer the pigment to surrounding keratinocytes via extensive dendrites. Melanin pigmentation is the principal determinant of hair and skin color. inhibiting apoptosis in melanocytes results in persistently pigmented keratinocytes, or hair coloration, and thus, delays or prevents hair greying which is due to loss of hair bulb melanocytes.

Methods of therapy include administering to the individual a substance, e.g., the tripeptide KGA, or an analog thereof, in a manner which permits contact of the substance with neurons of the CNS. For example, the pentapeptide CKGAC (SEQ ID NO: 3), or an analog thereof, can be chemically synthesized by methods well-known to one of skill in the art. The cysteine residues flanking the ends of the pentapeptide can be linked, e.g., by a disulfide bond, to maintain the conformation required for binding of the peptide to the $p75^{NTR}$, thus inhibiting, or preventing apoptosis. The length of the peptide can be longer than a pentapeptide, as long as the KGA, KGK or analog peptide is maintained in a configuration suitable for binding activity. For example, as described herein, cyclic peptides have been made with the amino acid sequences and CVGSNKGAIC (SEQ ID NO: 4) these peptide compete for $p75^{NTR}$ binding with beta-amyloid peptide.

Conversely, as a result of Applicants' discovery of the mechanism of apoptotic cell death in melanocytes and keratinocytes, methods are also provided that promote, apoptosis in these cells resulting in cell death. The promotion of cell death in keratinocytes may be desirable to decrease, or completely inhibit hair growth in specific areas on an individual. For example, the inhibition of facial hair growth, forearm hair growth or leg hair growth is often desirable. Thus, the methods described herein are also useful for human cosmetic purposes, e.g., for maintaining hair growth and coloration, or to remove unwanted hair.

Such inhibition of hair growth can be accomplished, for example, by the use of a blocking antibody that will block the binding of NGF to the p75 NGF-R expressed on keratinocytes. The blocking antibody (or an antibody fragment or peptide) will bind to the p75 NGF-R and thus prevent NGF from binding to the NGF-R. Thus, the NGF/p75 NGF-R mediated anti-apoptotic pathway is inhibited and cell death will be permitted, or enhanced after injury to the cells. For example, the specific area in which hair growth is to be inhibited can first be irradiated with UV light and then a composition comprising the blocking antibody can be applied (e.g., in a cream or ointment), resulting in apoptosis of injured keratinocytes and inhibition of hair growth. Alternatively, anti-trk antibodies can be used, as described herein, for activation of p75 nGF-R alone can initiate apoptosis. Furthermore, some ligands may induce apoptosis upon binding to p75 NGF-R. For example, if cell express high levels of p75 NGF-R, agregated β-amyloid peptide is described herein as binding to the p75 NGF-R and inducing apoptosis.

In another embodiment of the present invention, the invention relates to in vitro methods of using the methods and compositions described herein in cell culture to, e.g., prepare epidermal melanocytes or follicular keratinocytes for transplant to vertebrates. The methods of the present invention are also useful for identifying novel substances, capable of inducing hair growth or hair coloration or inhibiting hair growth in an individual. These methods can be based on Applicants' discovery of the apoptotic mechanism of death in melanocytes and keratinocytes. An in vitro method of evaluating p75 NGF-R/NGF mediated apoptosis can use, for example, C57BL-6 mouse skin specimens with synchronized hair follicles either in telogen or anagen, as described in Paus, R., et al., Br. J. Dermatol. 122:777–784 (1990), the teachings of which are incorporated herein by reference. These skin specimens, being larger than biopsies obtained from people, and having follicles in defined portions of the growth cycle are useful to investigate the relationship between NGF/NGF-R and growth state of the hair follicle. The necessary murine probes (cDNA and antibodies) are available. For example, anti-rat p75 NGF-R antibody is available from Accurate Chemical & Scientific Company (New York) and anti-mouse NGF antibody is available from Boehringer Mannheim Biochemicals (Indianapolis, Ind.). Rat NGF cDNA is described in Maisonpierre, P. C., et al., Science 247:1446–1451 (1990) and rat p75 NGF-R cDNA is described in Radeke, M. J. et al., Nature 325:593–597 (1987). A substance to be tested for anti-apoptotic activity in melanocytes can be evaluated in this, or another a melanocyte cell culture assay (e.g., as described in Example 1). Skin specimens or melanocytes can be maintained under conditions suitable for their proliferation and then exposed to UV irradiation. After irradiation, the substance to be tested for apoptotic activity can be added to the culture system. Subsequently, the cultured cells can be evaluated to determine whether cell death has been inhibited, or decreased.

Substances identified in this method are substances that specifically alter the apoptotic mechanism in melanocytes and kerantincytes. For example, substances that mimic nerve growth factor can be tested in an assay such as described above to evaluate their activity in inhibiting apoptosis. Additionally, substances identified and evaluated by this method can be peptides, organic molecules, small organic molecules, antibodies or antibody fragments.

Substances identified using methods described herein, found to bind p75 nerve growth factor receptor, or otherwise affect p75 nerve growth factor receptor, or found to initiate Bcl-2 expression, can be used in methods to induce hair growth, hair color or skin color. These methods comprise contacting epidermal cells, including basal layer melanocytes or follicular keratinocytes, of a vertebrate with an effective amount of a substance capable of inducing hair growth, hair color or skin color by inhibiting apoptosis in melanocytes or keratinocytes. An effective amount of such an identified substance is an amount effective to significantly decrease or completely inhibit apoptotic cell death in melanocytes and keratinocytes. The decrease of inhibition of apoptosis in melanocytes and keratinocytes can be evaluated using the methods described herein.

Various delivery systems are known and can be used to administer effective amounts of substances, such as naturally-occurring ligand or pseudo-ligand for p75 nerve growth factor receptor to inhibit apoptosis in melanocytes and keratinocytes. For example, encapsulation in liposomes, microparticles, microcapsules, expression by recombinant cells, receptor-mediated endocytosis, construction of a naturally-occurring or pseudo-ligand encoding nucleic acid as part of a retroviral or other vector can be used. In one embodiment, a liposome preparation can be used. The liposome preparation can be comprised of any liposomes which penetrate the stratum corneum and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. can be used.

Administration of the substances can also be, for example, by topical application to the epidermis of a vertebrate, such as a human, in a quantity sufficient to suppress apoptosis and prevent melanocyte or keratinocyte cell loss. The substance can be admixed in a pharmacological topical carrier such as a gel, an ointment, a lotion, a cream, or a shampoo and will include such carriers as water, glycerol, alcohol, propylene glycol, fatty alcohols, triglycerides, fatty acid esters, or mineral oils. Other possible topical carriers include, e.g., liquid petrolatum, isopropyl palmitate, polyethylene glycol, ethanol (95%), polyoxyethylene monolauriate (5%) in water, sodium lauryl sulfate (5%) in water. Other materials such as anti-oxidants, humectants, viscosity stabilizers, and similar agents may be added as necessary.

In addition, in certain instances, it is expected that the substances can be disposed within devices placed upon, in, or under the skin. Such devices include transdermal patches, implants, and injections which release the substance in such a manner as to contact the skin or hair follicle either by passive or active release mechanisms.

The delivery vehicle can also contain perfumes, colorants, stabilizers, sunscreens, or other ingredients. The substance can be applied, for example, topically to the epidermis at regular intervals, such as once or twice daily, in a suitable vehicle and at an effective concentration. Application can also be in a vehicle which specifically targets the appropriate cells (i.e., either epidermal melanocytes or epidermal keratinocytes). For example, a membrane marker specific for melanocytes, such as melanocyte stimulating hormone (MSH), can be incorporated into a liposome containing a substance that inhibits or decreases the transcription of the gene encoding the p75 NGF-R.

An effective amount of a substance that inhibits, decreases, or promotes apoptosis can be administered to an individual using any of the above-described methods. The actual preferred amounts of a ligand to be administered will vary according to the specific ligand being utilized, the particular compositions formulated, the mode of application, and the particular situs and vertebrate being treated. The concentration of the ligand effective to suppress apoptosis and to prevent epidermal melanocyte cell loss or epidermal keratinocyte cell loss, or to promote apoptosis, in a vertebrate, such as a human, can be determined using known, conventional pharmacological protocols.

The following examples more specifically illustrate the invention and are not intended to be limiting in any way.

EXAMPLE 1

Effect of UV Irradiation of Melanocytic Cell Death

Melanocytes or MM4 cells were plated in 60 mm diameter tissue culture dishes. Melanocytes were maintained in Medium 199 supplemented with 7% fetal bovine serum (FBS), 10 ng/ml epidermal growth factor (Collaborative Research), 10 g/ml insulin (Sigma), $10^{-9}$ microM triiodothyronine (Collaborative Research), 10 g/ml transferrin (Sigma), $1.4\times10^{-6}$ M hydrocortisone (Calbiochem), $10^{-9}$ microM cholera toxin (Calbiochem), and 10 ng/ml basic fibroblast growth factor (Collaborative Research) (basal melanocyte medium). MM4 cells were maintained in 55.3% DME, 27.6% L15, 15% FBS, 1% nonessential amino acids (GIBCO BRL), 2 mM glutamine and 10 g/ml insulin. After 24 hours, medium was replaced by phosphate buffered saline (PBS) and cells were irradiated using a 1 KW xenon arc solar simulator (XMN 1000-21, Optical Radiation Corp., Azuza, Calif.) with 5, 10, or 25 mJ/cm$^2$ UV through the petri dish plastic cover. Irradiance was adjusted to $4\times10^{-5}$ UV cm$^{-2}$ and metered with a research radiometer (model IL1700A, International Light, Newburyport, Mass.) fitted with a UVB probe at 285 Å 5 nm. After UV irradiation, cells were maintained in their respective media without FBS for 2 days (MM4 cells) or 3 days (melanocytes) and processed as indicated. Sham irradiated control cultures were handled identically but laced under a dark cloth adjacent to the UV beam.

Cells in 100 mm tissue culture dishes were washed with cold PBS and disrupted in lysis buffer pH8 (10 mM tris, 150 mM NaCl, 0.1 mM EDTA, 1% SDS, 200 g/ml proteinase K). After 15 hour incubation at 37%C, samples were extracted twice with phenol plus chloroform (1:1, V/V) and precipitated overnight with ethanol (2.5×volume) and 3 M sodium acetate (1/10×volume). The DNA was then digested with DNAse free ribonuclease (10 g/ml) for one hour at 37%C, separated on 1% agarose gel and stained with ethidium bromide. The size marker is 100 bp DNA ladder (STD) (Gibco/BRL, Gaithersburg, Md.). FIG. 1E shows that DNA fragmentation occurs in UV-irradiated but not sham irradiated MM4 cells.

Melanocytes were cultured on 8 chamber tissue culture slides (Nunc Inc., Naperville, Ill.) and were UV irradiated with 10 mJ/cm$^2$ as above. Four microM of propidium iodide (PI) was added to melanocyte cultures 24 hours after irradiation, for 5 minutes at 37%C. Cultures were washed with PBS and nuclei were analyzed using a Leitz confocal laser microscope (Leica, Deerfield, Ill.). FIG. 1F shows fragmentation of nuclear chromatin of UV-irradiated melanocytes. FIG. 1G shows homogenization of nuclear chromatin of UV-irradiated melanocytes.

Melanocytes were sham or UV irradiated with 10 mJ/cm$^2$ and 25 mJ/cm$^2$. Twenty-four hours after irradiation, 4 M of propidium iodide was added to cultures as above and cells were viewed with fluorescent phase contrast Nikon microscope. The number of fragmented or homogeneously stained nuclei versus nonstained nuclei was determined in several representative fields and expressed as a percent of total cells. A minimum of 130 cells were counted for each condition. FIG. 1H shows the percent PI-positive cells in melanocyte culture.

EXAMPLE 2

Nerve Growth Factor Enhances Survival of Human Melanocytes After Injury

Melanocytes were UV-irradiated three times on three consecutive days with 0, 5, 10 or 25 mJ/cm$^2$ doses. After each UV exposure, cells were placed until the next irradiation in fresh melanocyte medium containing 50 ng/ml NGF or diluent alone. FIG. 2A shows melanocyte yield after three daily UV irradiations of 0, 5, 10 and 25 mJ/cm$^2$.

Figure 2B:
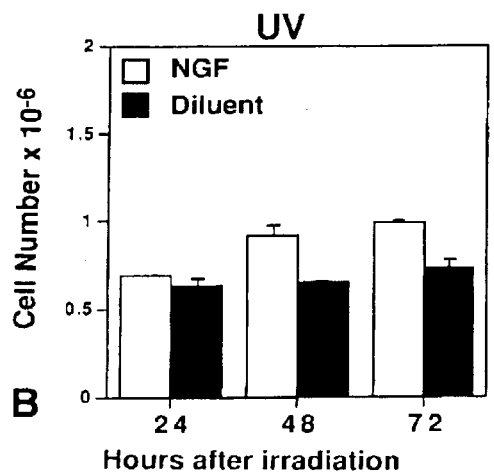
FIG. 2B is a bar graph depicting cell yields of MM4 after a single UV irradiation of 10 mJ/cm$^2$ and supplementation with 50 ng/ml NGF or diluent alone.
Figure 2C:
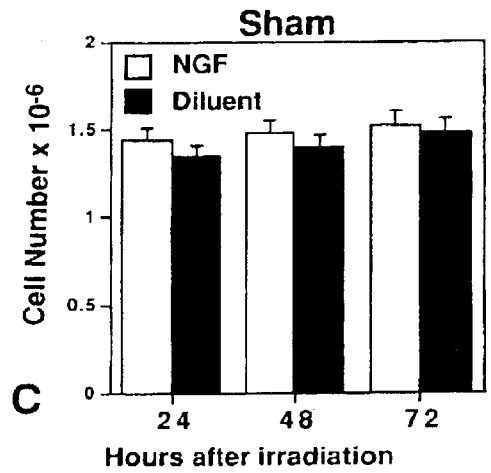
FIG. 2C is a bar graph depicting cell yields of MM4 after sham irradiation and supplementation with 50 ng/ml NGF or diluent alone.
Figure 2D:
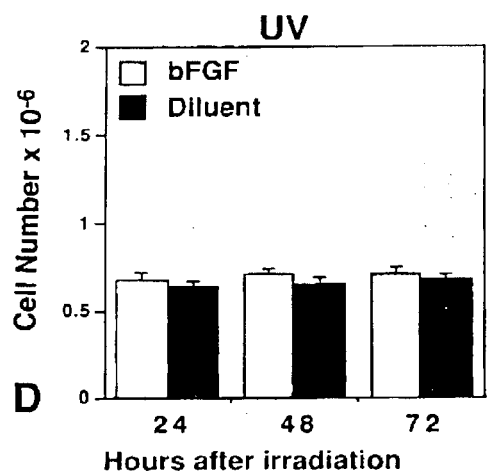
FIG. 2D is a bar graph depicting cell yields of MM4 after a single UV irradiation of 10 mJ/cm$^2$ and supplementation with 50 ng/ml bFGF or diluent alone.
Figure 2E:
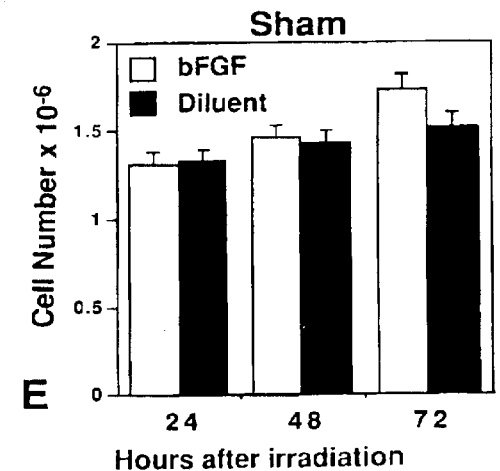
FIG. 2E is a bar graph depicting cell yields of MM4 after sham irradiation and supplementation with 50 ng/ml bFGF or diluent alone.

FIGS. 2B and 2D show MM4 cell yields 24–72 hours after a single UV irradiation of 10 mJ/cm$^2$. FIGS. 2C and 2e show MM4 cell yields 24–72 hours after sham irradiation. Cells in FIGS. 2B and 2C were supplemented with 50 ng/ml NGF or diluent alone. Cells in FIGS. 2D and 2E were supplemented with 50 ng/ml bFGF or diluent alone.

FIG. 2F shows the cell morphology of melanocytes after UV irradiation daily for three days with 10 mJ/cm$^2$ and supplemented with diluent alone. FIG. 2G shows the cell morphology of MM4 cells after UV irradiation once with 10 mJ/cm$^2$ and supplemented with diluent alone. FIG. 2H shows the cell morphology of melanocytes after UV irradiation daily for three days with 10 mJ/cm and supplemented with 50 ng/ml NGF. FIG. 2I shows the cell morphology of MM4 cells after UV irradiation once with 10 mJ/cm$^2$ and supplemented with 50 ng/ml NGF.

EXAMPLE 3

Nerve Growth Factor Rescues Injured Melanocytes Undergoing Apoptosis

Melanocytes or MM4 cells were plated as described in Example 1. After irradiation, melanocytes were maintained in basal melanocyte medium lacking FBS and hydrocortisone, with 50 ng/ml NGF or diluent alone (melanocyte medium). MM4 cells were maintained in DME supplemented with 50 ng/ml NGF or diluent alone.

Twenty-four hours after UV irradiation, cells supplemented with diluent alone (−) showed fragmentation, while DNA of cells supplemented with NGF (+) was not fragmented. The standard (STD) is 100 bp DNA ladder (Gibco/BRL). (See FIG. 3A).

Melanocytes were irradiated with 10 mJ/cm$^2$ or were sham irradiated as in Example 1 and then provided 50 ng/ml NGF or diluent alone. Twenty-four hours after irradiation, approximately 30% of diluent treated cells but only 12% of NGF supplemented cultures show positive nuclei.
That is, propidium iodide staining was positive in approximately 30% of nuclei in cultures not supplemented with NGF but in only 12% positive nuclei in NGF-supplemented cultures. (See FIG. 3B).

EXAMPLE 4

Melanocyte Expression of BCL-2 Protein After UV Injury

To determine if NGF induces Bcl-2 protein, MM4 cells were UV-irradiated with 10 mJ/cm$^2$ or sham irradiated and then supplemented with NGF or diluent alone as explained in Example 3. Twenty-four hours after irradiation, cells were washed with PBS and then detached with 0.5 mM EDTA and washed again with PBS. 10$^6$ cells were incubated with 3.25 g/ml mouse anti human Bcl-2 monoclonal antibody (DAKO Co., Carpinteria, Calif.) or with the same concentration of normal mouse IgG (Cappel, Organon Teknika Co., West Chester, Pa., USA) in PBS with 0.3% Saponin (Sigma, St, Louis, Mo.) for 2 hours at 4%C. After three washes with PBS, cells were incubated with fluorescein-conjugated goat anti-mouse IgG (1 hour at 4%C) (Cappel), washed four times in PBS, fixed with 0.1% fresh formaldehyde, and washed three times in PBS. Fluorescence intensity was determined using FACScan flow cytometer (Becton-Dickinson, San Jose, Calif.).

The results show that UV-irradiated FIG. 4A) or sham irradiated FIG. 4B) cells, cells supplemented with diluent alone, or sham irradiated cells supplemented with NGF had only low levels of Bcl-2 protein FACScan analysis. However, the Bcl-2 level was substantially higher in cells subjected to UV irradiation followed by NGF supplementation FIG. 4A). (−) mouse IgG control; (_) diluent alone; ( ... ) 50 ng/ml NGF.

Proteins from duplicate cultures analyzed by Western blotting confirmed Bcl-2 induction in UV irradiated NGF supplemented melanocytic cells (FIG. 4C). MM4 cells were extracted in RIPA buffer (50 mM Tris-HCl [pH 8.0], 0.15 M NaCl, 0.5% sodium deoxycholate, 1% Triton X-100) in the presence of one g/ml aprotinin and 75 g/ml phenylmethylsulfonyl fluoride, sonicated for 1–3 seconds and centrifuged. 45 g of protein per lane were separated on 12% SDS/PAGE and blotted onto nitrocellulose paper (overnight, 40V). Blots incubated with 3.25 g/ml anti-human Bcl-2 antibody (DAKO) reveal a band at the reported 25 kDa molecular weight: (+) 50 ng/ml NGF, (−) diluent alone.

EXAMPLE 5

Immunofluorescent Studies

Punch biopsies (6 mm diameter) can be obtained from scalps of patients for example, with patchy AA, alopecia totalis, alopecia universalis as well as uninvolved sites of AA patients and age matched controls and snap frozen for immunofluorescent studies. Immunostaining of fresh frozen tissues is compared with formaldehyde fixed tissues to determine if the antigen detection level is better in frozen sections. If the antibodies recognize formaldehyde fixed antigens with the same accuracy as non-denatured antigen, formaldehyde fixed tissues can be used for the immunofluorescent studies.

Figure 5D:
FIGS. 5D and 5E are photomicrographs showing p75 NGF-R levels in melanocytes and keratinocytes in anagen hairs of patients with alopecia areata.
Figure 5E:

Immunofluorescence was performed as described in Yaar, M., et al., Lab Invest. 58:157–162 (1988). Briefly, 4-microM thick vertical sections of biopsy samples were incubated with the first antibody overnight at 4%C. The second antibody applied was the appropriate fluorescein isothiocyanate conjugated antibody: either goat anti-rabbit or anti-mouse IgG (Cooper Biomedical). The second antibody was incubated for 30 minutes. Quantitation was performed by analysis of fluorescence intensity on the Leica Confocal microscope as described in Lu, K., et al., Proc. Natl. Acad. Sci. USA 89:3889–3893 (1992). FIGS. 5A and 5B show high levels of p75 NGF-R in melanocytes and bulbar keratinocytes of the outer root sheath in the lower portion of anagen hairs. FIG. 5C shows that p75 NGF-R levels were significantly reduced or absent melanocytes and keratinocytes of telogen hairs. FIGS. 5D and 5e show that p75 NGF-R levels were significantly lower or absent in melanocytes and keratinocytes in anagen hairs of AA patients.

EXAMPLE 6

Upregulation of P75 NGF-R in NGF Supplemented Melanocytic Cells Upregulates BCL-2 Protein To determine the role of p75 NGF-R in mediating NGF survival effect in melanocytic cells, MM4 cells were transfected with 5 ug DNA of PCMV5A expression vector carrying the p75 NGF-R cDNA, as well as, with 1 ug plasmid SV40 Neo carrying a neomycin resistant gene. Control cultures were transfected with 10 ug of SV40 Neo plasmid. Cultures were maintained in DME supplemented with 50–100 ng/ml G418 (geneticin), without serum, in the presence of 50 ng/ml NGF. Total cellular proteins were extracted in RIPA buffer (50 mM Tris-HCl, [pH 8.0], 0.15 M NaCl, 0.5% sodium deoxycholate, 1% Triton X-100) in the presence of 1 ug/ml aprotinin and 75 ug/ml phenylmethylsulfonyl fluoride, sonicated for 1–3 seconds and centrifuged. Blots were incubated with 3.25 ug/ml anti human BCL-2 antibody (DAKO).

Figure 6:
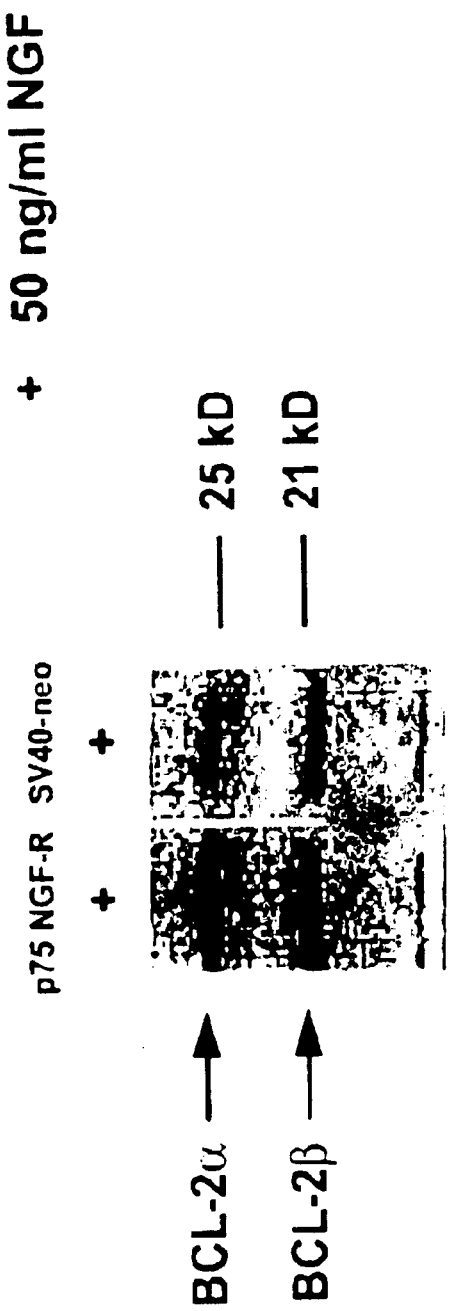
FIG. 6 is a photomicrograph showing the effect of nerve growth factor on BCL-2 induction in melanocytic cells transfected with p75 NGF-R.

The results shown in FIG. 6 demonstrate that melanocytic cells constitutively express the two known forms of the BCL-2 protein, BCL-2 alpha and BCL-2 beta. However, the levels of BCL-2 alpha and BCL-2 beta arc substantially higher in NGF supplemented cells transfected with p75 NGF-R as compared to NGF supplemented control cells, indicating that in the presence of NGF, higher levels of p75 NFG-R in cells that also express trk A, contribute to their survival.

EXAMPLE 7

Downregulation of P75 NGF-R in NGF Supplemented Melanocytic Cells Abrogated NGF Effect on Cells To further determine the role of p75 NGF-R in mediating NGF survival effect in melanocytic cells, 19 mer antisense and nonsense (scrambled) p75 NGF-R oligonucleotides were synthesized and were sulfurized to the phosphorothioate form. The antisense sequence was directed against the 5' end of the human p75 NGF-R coding region (Johnson, D., et al., Cell, 47:545–554 (1986)). The following sequences were used: Antisense 5' to 3' GGCACCTGC- CCCCATCGCC (SEQ ID NO: 5); Nonsense 5' to 3° CTC-CCACTCGTCATTCGAC (SEQ ID NO: 6) (negative control).

Melanocytes were maintained in Medium 199 supplemented with 5% fetal bovine serum (FBS), 10 ng/ml epidermal growth factor (Collaborative Research), 10 g/ml transferrin (Sigma), $1.4 \times 10^{-6}$ M hydrocortisone (Calbiochem), $10^{-9}$ M cholera toxin (Calbiochem, 10 ng/ml basic fibroblast growth factor (Collaborative Research) (basal melanocyte medium).

Near confluent cells were irradiated using a 1 KW xenon arc solar simulator (XMN 1000-21, Optical Radiation Corp., Azuza, Calif.) with 20 mJ/cm$^2$ UV through the petri dish plastic cover. Irradiance was adjusted to $4 \times 10^{-5}$ UV cm$^{-2}$ and metered with a research 20 radiometer (model IL1700A, International Light, Newburyport, Mass.) fitted with a UVB probe at 285 Å 5 nm. After UV irradiation, cells were trypinized and incubated in suspension at 37%C for 30 minutes with 10 uM antisense or nonsense p75 NGF-R oligonucleotides.

Figure 7:
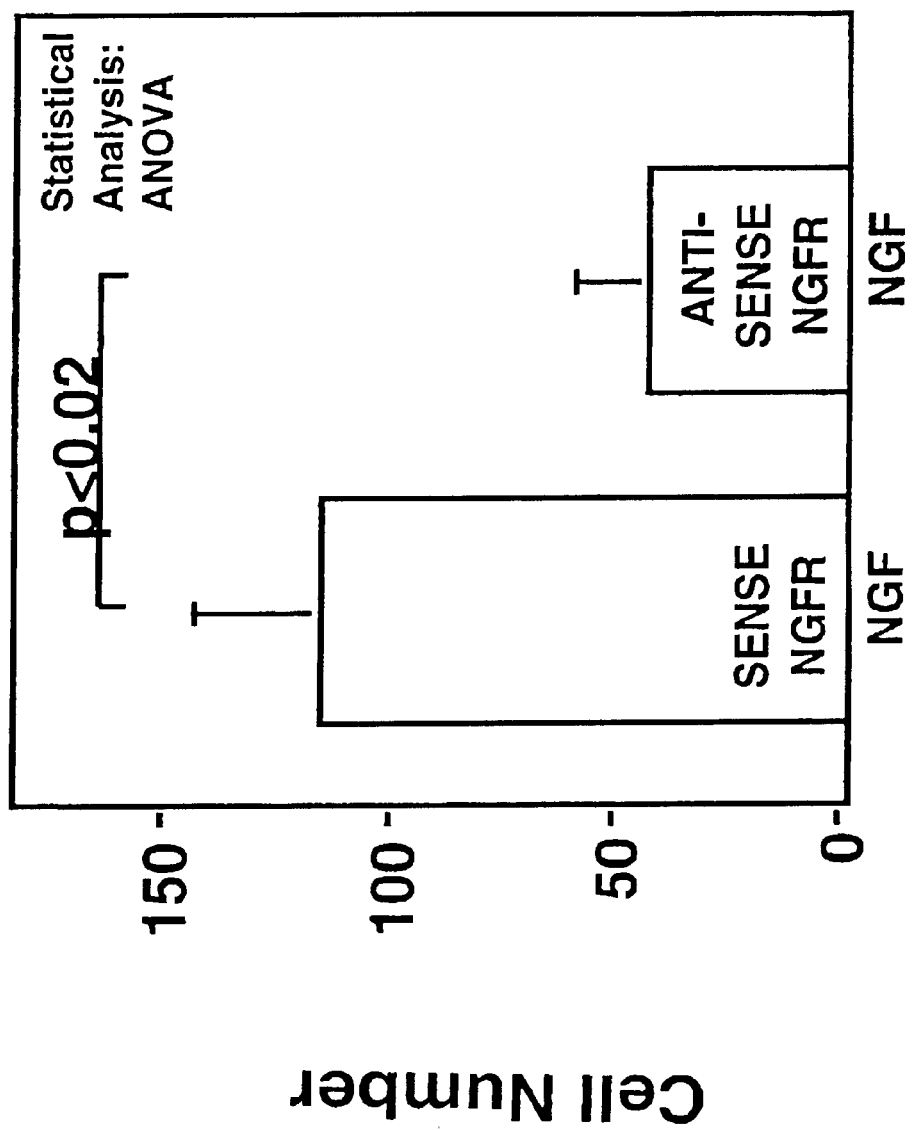
FIG. 7 is a bar graph depicting the downregulation of p75 NGF-R abrogates NGF effect on melanocyte survival. Cells were transfected with p75 NGF-R oligonucleotides and NGF-R expression was documented by indirect immunofluorescence.

After the initial 30 minute incubation cells were plated in 35 mm dishes in basal melanocyte medium without serum. Cells were supplemented with fresh oligonucleotides every 12 hours for 48 hours. Cells were visualized by phase contrast microscopy and pictures of representative fields were obtained. Cell yields were determined by counting cells in several representative fields. The results shown in FIG. 7 demonstrate that in the absence of p75 NGF-R (antisense NGF-R), NGF does not have an effect on melanocyte survival as compared to cells expressing p75 NGFR (sense NGF-R). This experiment confirms the role of p75 NGF-R in mediating the new growth factor effects in melanocytic cells.

EXAMPLE 8

BCL-2 Downregulation Abrogates NGF Protective Effect on UV Irradiated Melanocytic Cells Purified phosphorothioate oligonucleotides were purchased from Quality Controlled Biochemicals, Inc. (Hopkinton, Mass.). 19 mer oligonucleotides were designed based on the published human BCL-2 sequence (Tsujimoto, Y. and Croce, C. M., Proc. Natl. Acad. Sci. USA, 83:5214–5218 (1986)). The sequence chosen was directed against the end of the coding region starting 4 bases before the methionine initiation site. Nonsense oligonucleotides were used as control. Sequences used (all written 5' to 3'): Antisense CCCAGCGTGCGCCATCCTT (SEQ ID NO: 7); Nonsense CTCCCACTCGTCATTCGAC (SEQ ID NO: 8).

Figure 8:
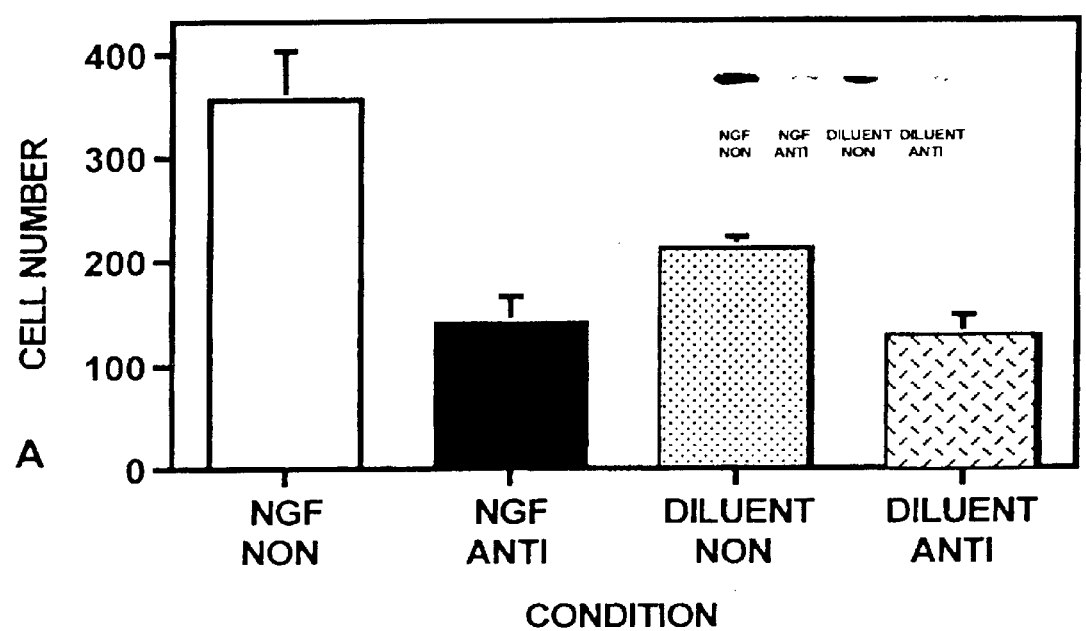
FIG. 8 is a bar graph depicting that BCL-2 downregulation abrogates NGF protective effect on UV irradiated melanocytic cells.

MM4 cells were maintained in 60 mm diameter tissue culture dishes in 55.3% DME, 27.6% L15, 15% FBS, 1% nonessential amino acids (GIBCO BRL), 2 mM glutamine and 10 g/ml insulin. Near confluent cells were UV irradiated with 10 mJ/cm$^2$. Immediately after irradiation cells were incubated with 10 uM antisense or nonsense BCL-2 oligonucleotides in suspension at 37%C for 30 minutes. Then cells were plated in tissue culture dishes in the presence or absence of NGF (50 ng/ml). Cells were supplemented with fresh oligonucleotides every 12 hours. Cell yield and BCL-2 level were determined 48 hours after irradiation. Cell yield was determined by counting cells in at least three representative field per each condition. FIG. 8 shows the results of a Western blot demonstrating that in the presence antisense BCL-2 oligonucleotides BCL-2 levels are almost undetectable. Cell yields of UV irradiated cultures supplemented with NGF and nonsense oligonucleotides (white bar) are significantly higher as compared to nonsense supplemented cultures provided with diluent alone (dotted bar) (p<0.007, ANOVA). Cell yields of NGF supplemented cultures treated with BCL-2 antisense oligonucleotides (black bar) are significantly lower than NGF supplemented cultures provided with nonsense oligonucleotides (white bar) demonstrating complete abrogation of NGF effect on the cells (p<0.003, ANOVA). In diluent supplemented culture yields of nonsense treated cells (dotted bar) were significantly higher than antisense treated cells (dashed bar) (p<0.004, ANOVA). Morphologic appearance of MM4 cells confirmed the numerical cell yield data This experiment demonstrated that BCL-2 protein is required for melanocytic survival after UV irradiation and that NGF affects melanocytic cell survival by upregulating their BCL-2 level.

EXAMPLE 9

Effect of UV Irradiation on Keratinocyte Cell Death

Keratinocytes were plated in 60 mm diameter tissue culture dishes in MCDB153 supplemented with epidermal growth factor (0.1 ng/ml human recombinant), insulin (5 microg/ml), hydrocortisone (0.5 microg/ml, calcium (0.15 mM), bovine pituitary extract (BPE), (2 ml per 500 ml medium), gentamicin (50 microg/ml), and amphotericin-B (50 ng/ml) (karetinocyte basal medium). Preconfluent cells were irradiated in phosphate buffered saline PBS) using a 1 KW xenon arc solar simulator (XMN 1000-21, Optical Radiation Corp., Azuza, Calif.) with 15 or 25 mJ/cm$^2$ UV through the petri dish plastic cover as described in Example 7. After UV irradiation, cells were maintained in their basal medium 3 days and processed as indicated. Sham irradiated control cultures were handled identically but placed under a dark cloth adjacent to the UV beam.

Cells were washed with cold PBS and disrupted in lysis buffer pH8 (10 mM tris, 150 mM NaCl, 0.1 mM EDTA, 1% SDS, 200 g/ml proteinase K). After 15 hour incubation at 37%C, samples were extracted twice with phenol plus chloroform (1:1, V/V) and precipitated overnight with ethanol (2.5×volume) and 3 M sodium acetate (1/10×volume). The DNA was then digested with DNAse free ribonuclease (10 microg/ml) for one hour at 37C, separated on 1% agarose gel and stained with ethidium bromide. The data show that DNA fragmentation, characteristic of apoptotic cell death, occurs in UV-irradiated but not sham irradiated keratinocytes.

EXAMPLE 10

Nerve Growth Factor Enhances Survival of Human Keratinocytes After Injury

Figure 9A:
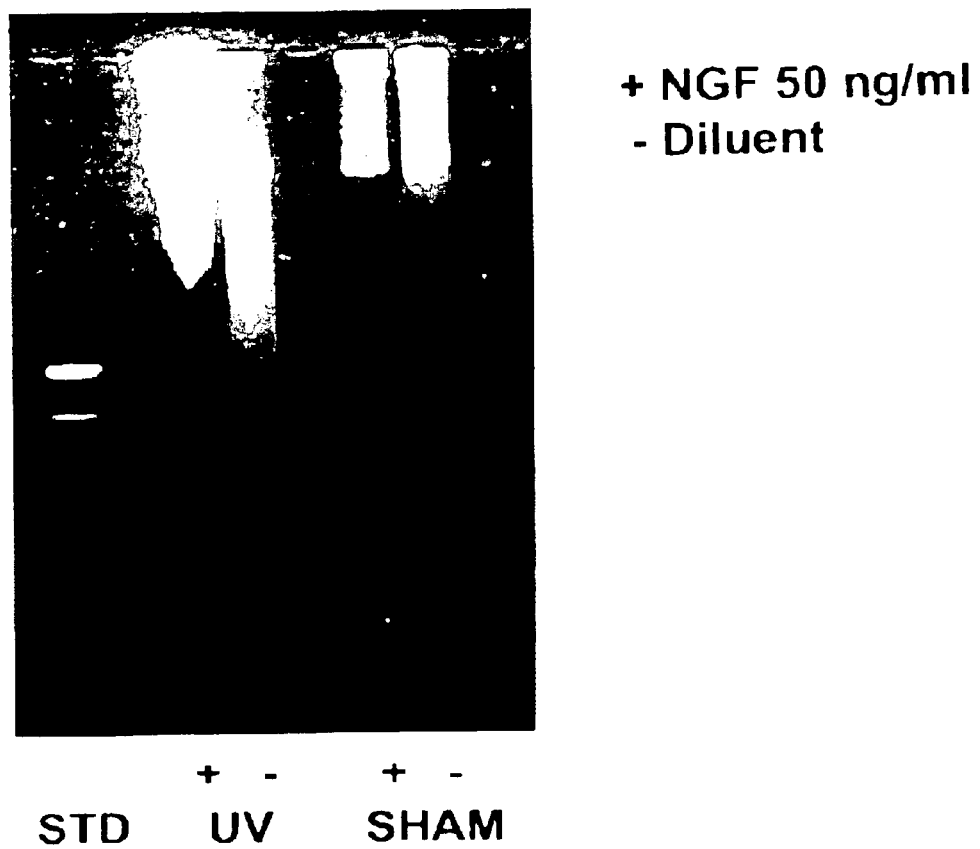
FIG. 9A is a photomicrograph showing the effect of UV irradiation and nerve growth factor supplementation on keratinocyte apoptosis.
Figure 9B:
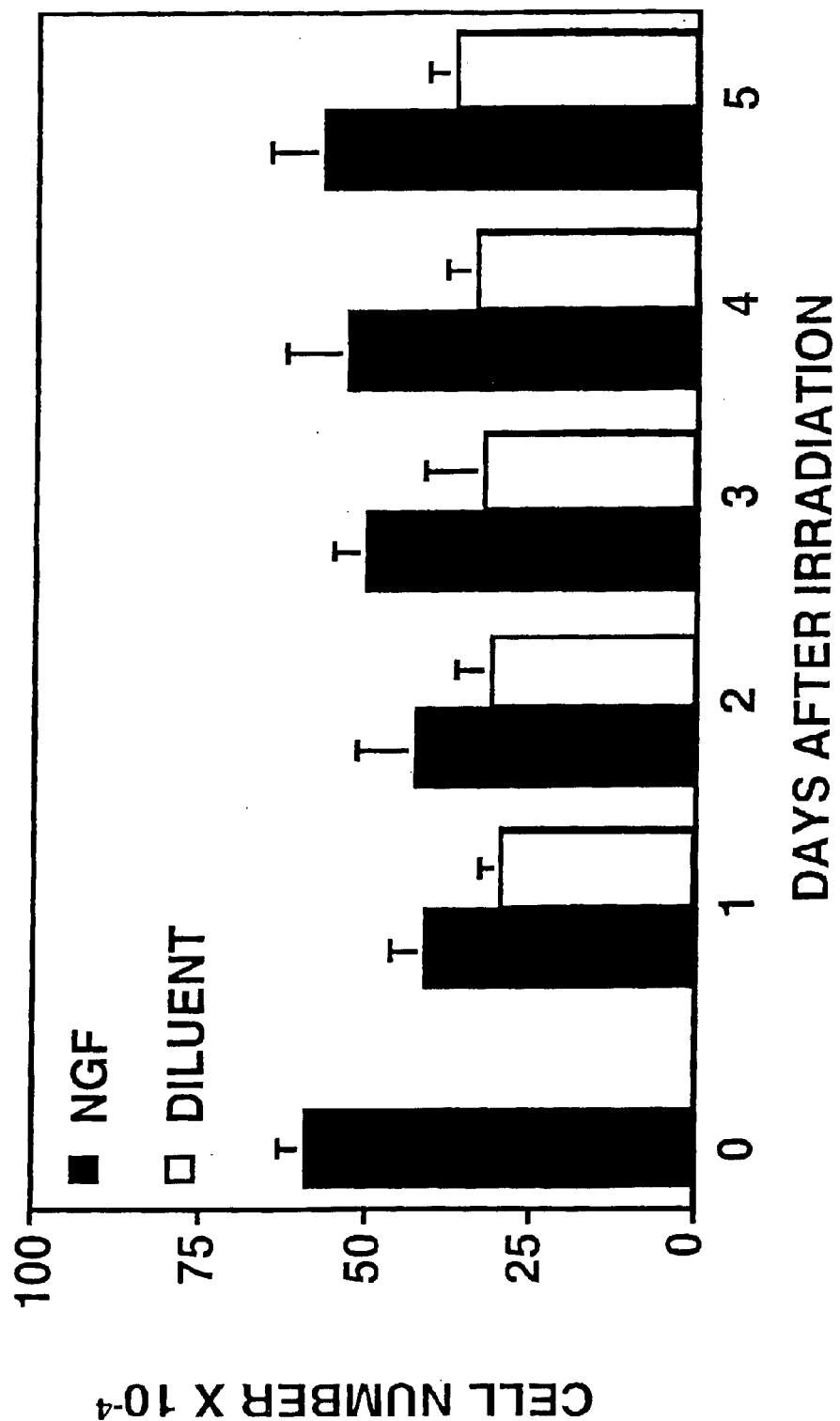
FIG. 9B is a bar graph depicting the effect of UV irradiation and nerve growth factor supplementation on keratinocyte survival.

Keratinocytes were UV-irradiated as in Example 9. After irradiation cells were placed in fresh keratinocyte medium containing 50 ng/ml NGF or diluent alone. DNA fragmentation was determined as in Example 9. FIG. 9A shows that UV irradiated keratinocytes supplemented with diluent alone (−) display the characteristic DNA fragmentation, while DNA of UV irradiated cells supplemented with NGF (+) is not fragmented. The standard (STD) is 100 bp DNA ladder (Gibco/BRL). Keratinocyte yield determined daily for 5 days as shown in FIG. 9B demonstrates that within 24 hours there is a 50% decrease in cell yield in cultures provided with diluent alone but on 30% decreases in cultures provided with NGF. UV irradiated keratinocytes were growth arrested as expected. However, cell yields of keratinocytes maintained in NGF supplemented medium increased by 40% within the 5 days of the experiment, suggesting that NGF is a mitogen for keratinocytes as well as a survival factor. This experiment demonstrates that, similar to melanocytes, NGF is a survival factor for keratinocytes. Furthermore, the experiment suggests that NGF might be a mitogen for keratinocytes as well.

EXAMPLE 11

Keratinocyte Expression in BCL-2 Protein After NGF Deprivation

To determine if NGF affects BCL-2 protein level in keratinocytes, cells were maintained in Keratinocyte basal medium until 60–80% confluent. Then cells were provided medium lacking BPE to eliminate exogenous NGF. Duplicate cultures were provided 50 ng/ml NGF or diluent alone.

Figure 10:
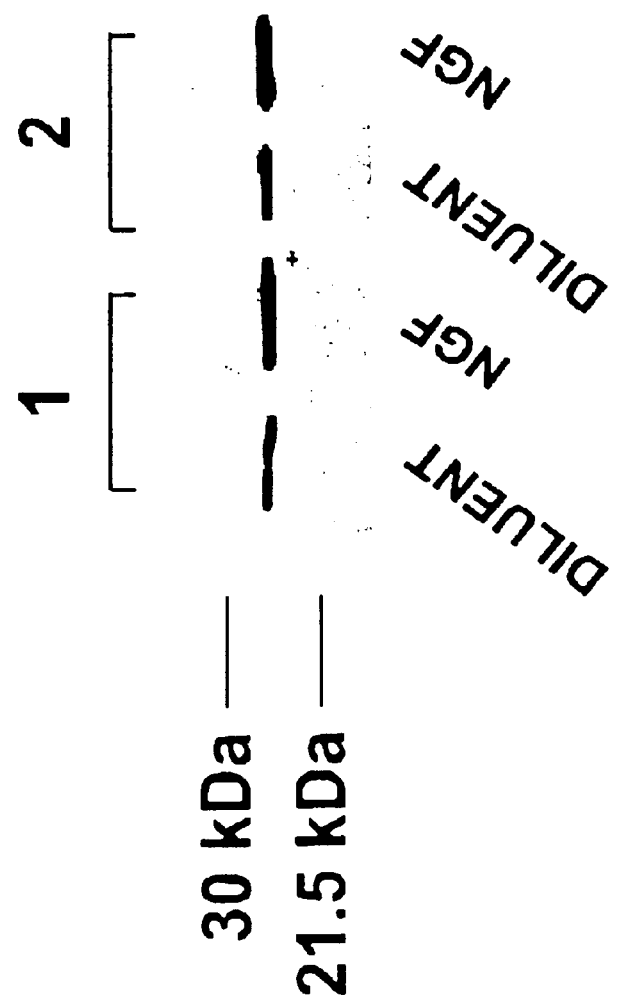
FIG. 10 is a photomicrograph showing the effect of nerve growth factor depletion of BCL-2 level in keratinocytes.

Total keratinocyte proteins were extracted, and BCL-2 levels were determined by Western blot analysis as in Example 6. FIG. 10 shows that within 24 hours of NGF depletion decreased BCL-2 level was detected in diluent supplemented keratinocytes as compared to NGF supplemented cells. Similar findings were observed at 48 hours. This experiment demonstrates that NGF contributes, at least in part, to BCL-2 maintenance keratinocytes.

EXAMPLE 12

The Effect of Beta-amyloid on Normal Human Melanocytes

To determine the effect of beta-amyloid on normal human melanocytes, cultures were supplemented with increasing concentrations (0.025–50 uM) of HPLC-purified beta-amyloid fragment corresponding to amino acids 1–40. A peptide containing the first 40 amino acids synthesized in reverse order (40–1) was used as a negative control.

Melanocytes were maintained in serum free Medium 199 (Gibco BRL Gaithersburg, Md.) supplemented with epidermal growth factor (10 ng/ml) (Collaborative Research), insulin (10 microg/ml) (Sigma), triiodothyronine ($10^{-9}$ microM)(Collaborative Research), transferrin (10 g/ml) (Sigma), hydrocortisone ($1.4 \times 10^{-6}$ microM) (Calbiochem), cholera toxin ($10^{-9}$ microM) (Calbiochem) and basic fibroblast growth factor (basic FGF) (10 ng/ml) (Collaborative Research). Two days after plating cells were supplemented with increasing concentrations of -amyloid 1–40 or the control peptide 40–1 (0–50 microM) (Bachem California, Torrance, Calif.). Cell yields determined three days after addition of beta-amyloid show a dose dependent decrease of cell yield in cultures maintained with the 1–40 peptide. No effect on cell yield was observed in cultures maintained with the control 40–1 peptide.

Melanocytes maintained in the presence of 25–30 uM beta-amyloid 1–40 showed a 59% plus/minus 17% decrease in cell yield as compared to cell yield before -amyloid addition that is considered to be 100%. Cell yield of duplicate cultures maintained in the presence of the control 40–1 peptide showed 8% plus/minus 32% increase in cell yield ($p<0.02$, paired t test).

Melanocytes maintained in the presence of the 40–1 control peptide have a typical bipolar to polygonal morphology. The majority of the melanocytes maintained in the presence of the 1–40 peptide are rounded and detaching from the dish surface.

Regression analysis showed significant decrease in cell yield with increasing concentrations of beta-amyloid 1–40 ($R^2=0.8475$, $p<0.00001$) but no significant effect on cell yield of beta-amyloid 40–1 ($R^2=0.06$, $p=0.44$). In a total of four experiments, within 3–5 days beta-amyloid 1–40 decreased melanocyte yield by >50% ($p<0.02$; paired t test) while the control 40–1 beta-amyloid peptide at the same concentrations had no effect on cell yield.

EXAMPLE 13

Effect of Beta-amyloid 1–40 on Melanocyte Plaque Formation

Melanocyte cultures, cultured as described above in Example 12, were also evaluated for plaque formation. In some cultures the development of plaque-like structures consisting of increasingly large congregations of dying melanocytes was noted, reminiscent of the senile plaques described in the brains of patients with Alzheimer's disease.

EXAMPLE 14

Effect of Beta-amyloid and NGF on Melanocytes

In neurons, the protein product of the proto-oncogene Bcl-2 delays the onset of apoptosis triggered by a variety of stimuli, while overexpression of a Bcl-2 associated protein (Bax) accelerates this cell death.

To investigate the mechanism of -amyloid-mediated melanocyte death, Bax levels in melanocytes treated with 25 uM of 1–40 or 25–35-amyloid peptides was examined. Within 4 days of treatment, Bax was induced 3 fold in melanocytes stimulated either with the beta-amyloid 1–40 or 25–35 fragments as compared to melanocytes treated with the 40–1 control fragment or an irrelevant HPLC purified protein of similar size.

Melanocytes were maintained as above. Four days after addition of 25 microM of beta-amyloid fragments 1–40 40–1 or 25–35; or 25 microM of HPLC-purified bovine corticotropin releasing factor (CRF) (Bachem Calif.) (MW 4.7 kD) as an additional negative control, cells were extracted in RIPA buffer (50 mM Tris-HCl [pH 8.0], 0.15 M NaCl, 0.5% sodium deoxycholate, 1% Triton X-100) in the presence of 1 microg/ml aprotinin and 75 microg/ml phenylmethylsulfonyl fluoride (PMSF), sonicated for 1–3 seconds and centrifuged. 40 microg of protein per lane were separated on 12% SDS/PAGE and blotted onto nitrocellulose paper (overnight, 25C). To verify equal loading a duplicate 13% SDS/PAGE was performed and stained with Coomasie Blue R250 stain. Blots were incubated with anti-Bax antibody (1:1000 dilution) (primary antibody), followed by horseradish peroxidase-conjugated goat anti-rabbit IgG (secondary antibody) (1:500 dilution) (Bio-Rad Laboratories, Hercules, Calif.). Bound antibodies were detected using enhanced chemiluminescence kit (Amersham Corp.). Autoradiograms were scanned into a Macintosh II is computer using the Ofto TM program (Light source Computer Images, Inc.). Scan analysis was performed with manual definition of bands using Scan Analysis TM 68000 program (Biosoft, Cambridge, UK).

Beta-amyloid peptides 1–40 and 25–35 increased Bax level as compared to the 40–1 peptide (270% and 160%, respectively).

EXAMPLE 15

Effect of NGF on Beta-amyloid Induced Cell Death

Nerve growth factor (NGF) has been reported to delay melanocyte apoptosis by upregulating the levels of Bcl-2

(Zhai, S., et al. Exp. Cell. Res It was investigated whether NGF supplementation protects melanocytes from beta-amyloid-induced cell death. Addition of NGF to beta-amyloid-supplemented melanocytes enhanced cell yields within 3–5 days and greatly improved the morphology of surviving cells in most donors, although degree of protection was variable among donors. Preliminary data suggest that NGF supplementation decreases the beta-amyloid-induced Bax upregulation and increases Bcl-2 levels in the cells suggesting that NGF interferes with beta-amyloid-mediated signal transduction.

Melanocytes were maintained as above in hormone supplemented medium lacking hydrocortisone. Cells were supplemented with 25 microM of beta-amyloid 1–40 in the presence of 50 ng/ml NGS or diluent.

Photographs of representative fields were obtained and the percent of the live cells (spread) was determined 48 hours after addition of beta-amyloid and NFG or beta-amyloid and diluent. In the presence of beta-amyloid and diluent 77±8.5% appeared spread as compared to 96±1.4% in cultures supplemenbetated in beta-amyloid and NGF. In cultures not provided -amyloid and diluent even the cells that were still spread on the dish surface were vacuolated and generally did not appear as healthy as cells in NGF supplemented cultures.

Beta-amyloid exposed melanocytes in the absence of NGF are dying, while in the presence of NGF the cells appear healthy and spread on the dish surface. At least 400 cells were counted in each condition.

EXAMPLE 16

Beta-amyloid Binds the p75 Nerve Growth Factor Receptor

To determine if beta-amyloid binds $p75^{NTR}$, $^{125}I$ 1–40 beta-amyloid peptide was added to permanently transfected cultured fibroblasts that over express $p75^{NTR}$ ($p75^{NTR}$ NIH 3T3 cells) (Dobrowsky, T. T., et al., Science, 265:1596 (1994) in the presence of disuccinimidyl suberate to cause cross linking of closely associated proteins. Cells were then immunoprecipitated with anti $p75^{NTR}$ antibodies or an irrelevant mouse IgG. Autoradiograms revealed a protein band of 75–80 kD in size only in lysates immunoprecipitated with anti $p75^{NTR}$ antibodies. Competition analysis of $^{125}I$ 1–40 beta-amyloid in the presence of increasing concentrations of unlabeled NGF showed that 1–40 beta-amyloid could be competed off by NGF. However, residual $^{125}I$ 1–40 binding suggests that 1–40-amyloid may have an additional cell surface receptor, perhaps the recently identified serpin-enzyme complex receptor.

Results indicate that $p75^{NTR}$ is a receptor for beta-amyloid, a peptide that is reported to be secreted into the medium of normal cells in high picomolar to low nanomolar concentrations.

$p75^{NTR}$-NIH 3T3 cells were maintain in DMEM supplemented with 10% FBS in the presence of penicillin (45 ng/ml), streptomycin (68 ng/ml), and hygromycin B (17.5 ng/ml). At 80% confluence cells were lifted from the dish with EDTA and incubated in suspension with 5 Ci $^{125}I$ beta-amyloid 1–40 at 4C for 1 hour in DMEM. After incubation, 1 mM of disuccinimidyl suberate was added for 30 minutes. Following centrifugation cells were lysed with RIPA buffer (50 mM Tris HCl, pH 8.0, 0.15 microM NaCl 0.5% sodium deoxycholate 4, 5 mM $MgCl_2$, 1% Triton x-100, 1 mM phenylmethylsulfonylfluoride [PMSF], and 1 microg/ml aprotinin), sonicated for 1–3 seconds and immunoprecipitated with anti $p75^{NTR}$ antibodies (mouse monoclonal IgG1, Cedarlane Laboratories Ltd., Ontario, Canada) or mouse IgG as control for 16 hours at 40C in the presence of 15 microl of protein G plus protein A agarose and 1M NaCl adjusted to pH 8.0. After several washes with 20 mM Tris HCl, pH 8.0, 1M NaCl, 5 mM $MgCl_2$, 0.2% Triton X-100 and 1 mM PMSF, immunoprecipitates were separated over 8% PAGE and subjected to autoradiography. A band of 75–80 kD molecular weight was present only in lysates inmmunoprecipitated with anti $p75^{NTR}$ antibodies and not lysates inmmunoprecipitated with irrelevant mouse IgG.

$p75^{NTR}$-NIH 3T3 cells were incubated for 2 hours at 40C in binding medium (DMEM, 10 mM hepes, 0.1 mg/ml cytochrome C, 0.01% Tween 80, 1 mg/ml BSA) with $^{125}I$ beta-amyloid 1–40 and increasing concentrations of NGF (0–100 ng/ml). After rinsing in PBS cells were lysed in 1N NaOH and equal amounts of protein from cell lysates were subject to counting. A concentration dependent inhibition of $^{125}I$ beta-amyloid binding by NGF was observed with a maximum of 38% inhibition at NGF concentrations of 100 ng/ml and statistically comparable binding at 25 ng/ml.

EXAMPLE 17

Figure 11:
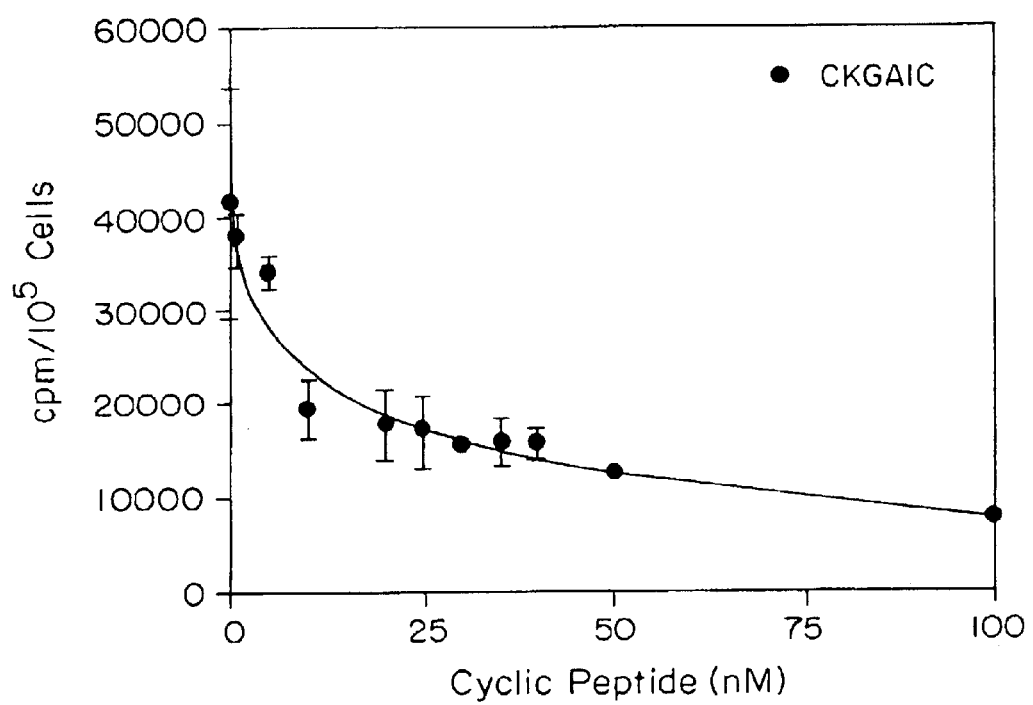
FIG. 11 is a graph of experimental results showing competition for binding to p75$^{NTR}$ by CKGAIC (SEQ ID NO:10) peptide and beta-amyloid.

KGA-containing Peptides Competitively Inhibit Beta-amyloid Binding to $p75^{NTR}$ $p75^{NTR}$-NIH-3T3 cells were incubated in suspension at 4%C for 4 hours with 0.5 $Ci^{125}I$ beta-amyloid 1–40 and increasing concentrations (0–400 nM) of the cyclic peptide CVGSNKGAIC (SEQ ID NO: 4). Lysates from $1.5 \times 10^5$ cells were subjected to counting. As shown in FIG. 11, concentration dependent inhibition of $^{125}I$ beta-amyloid 1–40 binding by the cyclic peptide was observed with 50% inhibition was observed at the expected 25 nM cyclic peptide concentration. This experiment demonstrates the cyclic peptide can compete with beta-amyloid 1–40 for binding to the $p75^{NTR}$ receptor.

EXAMPLE 18

Figure 12A:
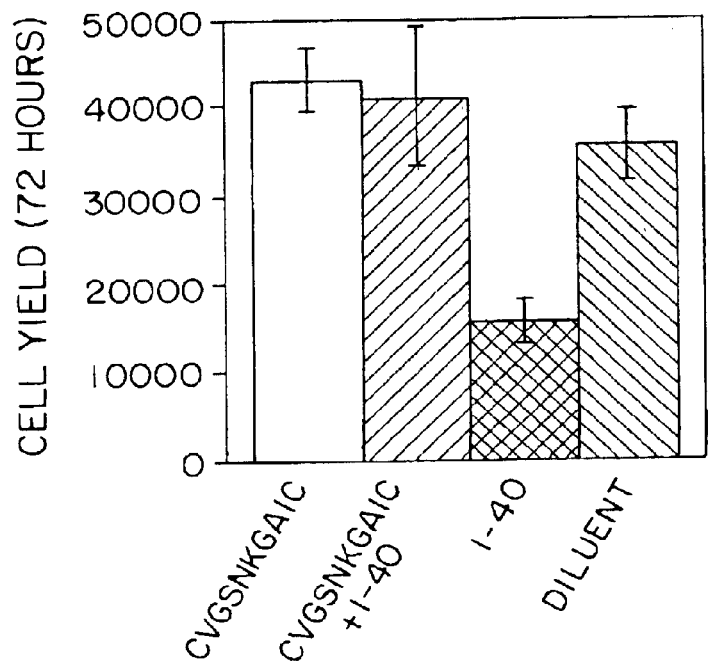
FIG. 12A is a bar graph depicting abrogation of -amyloid mediated apoptosis by a KGA-containing decapeptide.
Figure 12B:
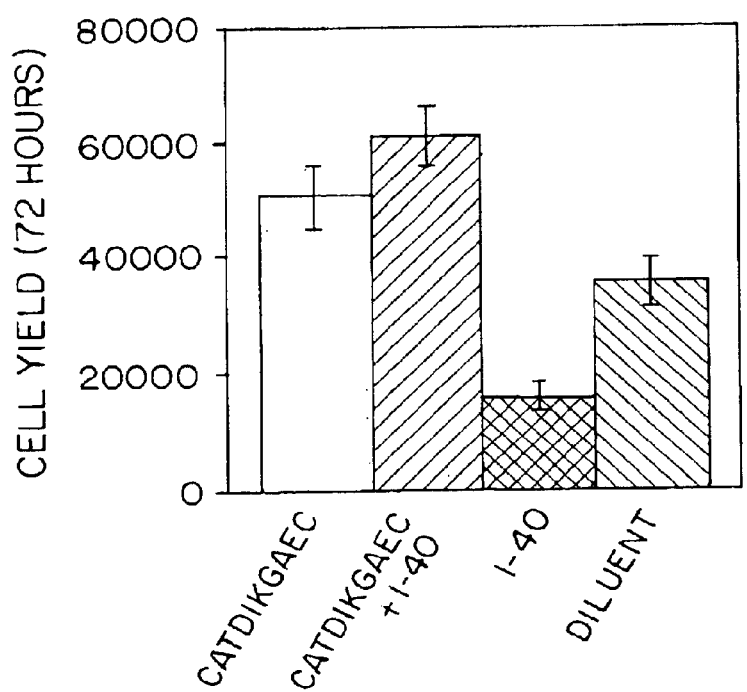
FIG. 12B is a bar graph depicting abrogation of beta-amyloid mediated apoptosis by a KGA-containing decapeptide.
Figure 12C:
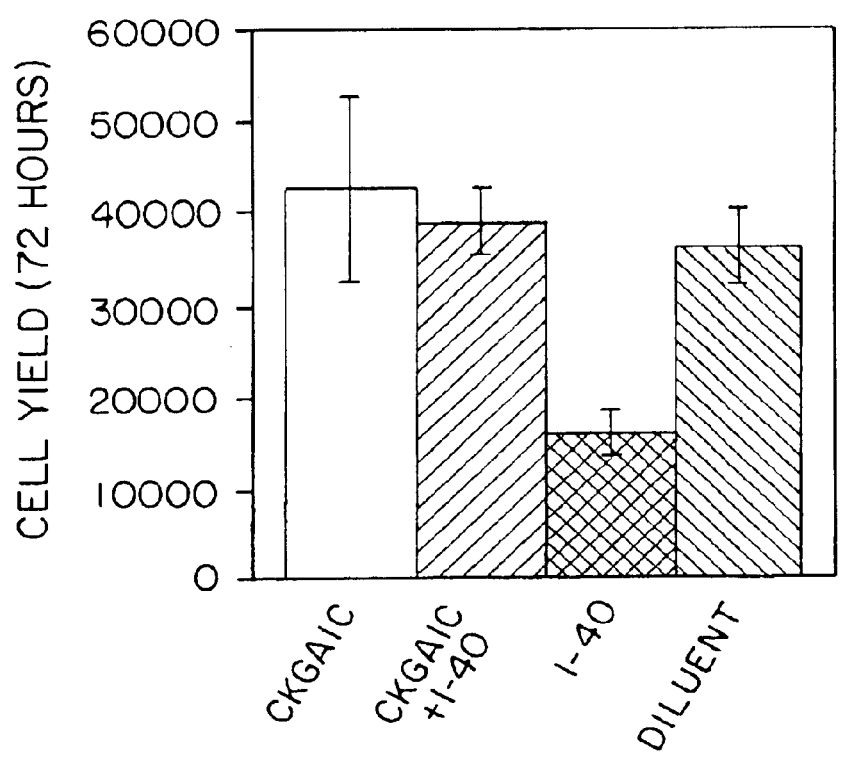
FIG. 12C is a bar graph depicting abrogation of beta-amyloid mediated apoptosis by a KGA-containing hexapeptide.

Effect of KGA-containing Peptides on Cell Survival $p75^{NTR}$-NIH 3T3 cells were maintained in DME supplemented with 10% calf serum until 80% confluent. The cells were washed and incubated in serum free DME containing transferrin (5 microg/ml) and insulin (5 microg/ml). Triplicate dishes were supplemented with diluent or preaggregated beta-amyloid 1–40 (250 nM) as positive and negative controls, respectively. FIG. 12A shows the results from triplicate dishes supplemented with cyclic decapeptide CVGSNKGAIC (250 nM, SEQ ID NO:4) alone or together with preaggregated beta-amyloid 1–40 (250 nM). FIG. 12B shows the results from triplicate dishes supplemented with cyclic 250 nM decapeptide CATDIKGAEC (SEQ ID NO:9) alone or together with preaggregated beta-amyloid 1–40 (250 nM). FIG. 12C shows the results from triplicate dishes supplemented with 250 nM cyclic hexapeptide CKGAIC (SEQ ID NO:10) alone or together with preaggregated beta-amyloid 140 (250 nM). After 72 hours, cells were rinsed in PBS and cultures were incubated in 0.25% trypsin at 37° C. Cell yields were determine using a particle counter. Cell yields in cultures supplemented with each cyclic peptide and beta-amyloid were significantly higher than yield of cultures supplemented with beta-amyloid alone (p<0.01 CVGSNKGAIC (SEQ ID NO:4), p<0.0002 CATDIKGAEO (SEQ ID NO:9), p<0.002 CKGAIC (SEQ ID NO:10);

non-paired t test comparing the effect of beta-amyloid and peptide to beta-amyloid alone. Test was performed separately for each group).

EXAMPLE 19

Elucidation of Apoptotic Signaling Pathways Following Activation of the 75 kD Neurotrophin Receptor The 75 kD neurotrophin receptor (p75) is strongly expressed in keratinocytes, melanocytes and neurons and has been implicated in apoptosis of these cells under certain conditions. When neurotrophins activate p75 together with receptors of the Trk family, p75 evokes a survival signal. However, when p75 is activated alone, it may signal for apoptosis by stimulating within minutes sphingomyelin turnover and ceramide generation. Still, the sequence of events linking p75 stimulation to ceramide generation and apoptosis remain largely unknown.

Figure 13:
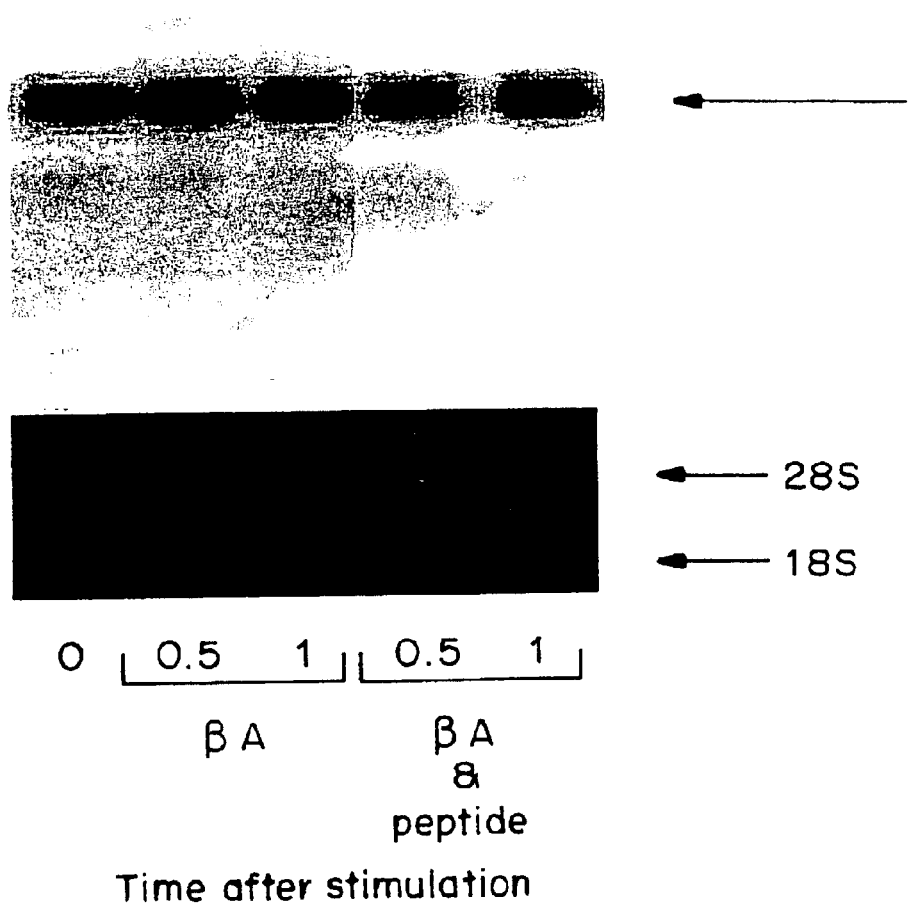
FIG. 13 is a photograph of a Northern blot analysis showing the results of an experiment demonstrating a rapid upregulation of c-jun transcripts in cultures stimulated with Aβ but not in cultures pre-treated with cyclic peptide.

To investigate p75 early signaling, NIH-3T3 cells engineered to constitutively express human p75 (3T3-p75), were stimulated with a known p75 ligand β amyloid (βA), and the distribution of p75 on the cell surface was analysed using immunohistochemistry and confocal laser microscopy. Within minutes βA-treated cultures displayed aggregation of p75, while the baseline, homogeneous cell surface distribution of p75 did not change in diluent treated cultures. Furthermore, 3T3-p75 stimulated with βA in the presence of a bifunctional crosslinker and then reacted with anti p75 antibodies displayed on western blots in addition to the expected 75 kD band also a ~220–230 kD band, consistent with receptor trimerization, as reported for other apoptotic signaling pathways. Moreover, similar to signaling initiated by the apoptotic TNF-α and Fas receptors, βA activation of p75 strongly induced the transcription of the immediate early c-jun mRNA, stimulated the stress-activated c-Jun $NH_2$-terminal kinase (JNK) as measured by phosphorylation of its substrate [GST-cJun (1–79)], activated caspase-3 to cleave its substrate [poly-(ADP ribose)polymerase], and induced the characteristic DNA fragmentation into multimers as measured by TUNEL analysis and DNA ladder formation. (FIG. 13)

To determine if the initial step of p75 aggregation is required for initiation of apoptosis, 3T3-p75 were pretreated with an HPLC purified cyclic peptide (CATDIKGAEC) (SEQ ID NO:9) that binds the ligand binding site of p75, and then cultures were stimulated with βA or with diluent alone. The cyclic peptide inhibited p75 aggregation, decreased c-jun transcription that was otherwise prominent in UV-irradiated diluent-treated keratinocytes. These data identify for the first time the initial signaling events that follow p75 activation and suggest that signaling through p75 requires receptor aggregation.

EXAMPLE 20

Regulation and Activation of the 75 kD Neurotrophin Receptor in Human Melanocytes Melanocytes (MC) express the 75 kD neurotrophin (NT) receptor (p75) that binds all Nts. In the presence of Trk receptors, NTs bind both p75 and Trk and signal through Trk. However, data suggest that even when p75 is present alone, it may be activated to signal cell survival or apoptosis. Because in neural crest cells p75 expression is down-regulated by increased cyclic AMP (cAMP) levels that occur after nerve injury, it was investigated whether p75 is similarly regulated in MC.

MC were stimulated with growth factor-containing medium supplemented with forskolin (50 μM) or IBMX (100 μM) that increase cAMP levels. In diluent treated cells, p75 mRNA increased within 24 hours but forskolin and IBMX substantially inhibited this upregulation. To determine if ultraviolet (UV) irradiation that induces cutaneous injury upregulates p75, MC were sham- or UV-irradiated with solar simulated light (30 mJ/cm$^2$, metered at 285+5 nm). After an initial down-regulation within 4 hours, at 24 and 48 hours p75 mRNA was strongly induced in UV- vs sham-irradiated cells. Furthermore, 48 hours after irradiation, cAMP levels were >70% decreased in UV- vs sham-irradiated cells.

To investigate p75 signal transduction, it was first determined by RT-PCR that trkA and trkC are not expressed in MC maintained in choleragen/TPA-free medium. MC were incubated with 10 ng/ml nerve growth factor (NGF) or neurotrophin-3 (NT-3) for 30 minutes and c-Jun amino terminal kinase (JNK) activation was determined. Compared to diluent or NT-3, NGF substantially induced phosphorylation of GST-c-Jun(1–79). Moreover, pre-incubation of MC with a cyclic peptide CATDIKGKEC (SEQ ID NO:9) that binds p75 abrogated JNK activation in NGF stimulated cells. Furthermore, within 3 hours p75 activation by NGF, but not by NT-3, lead to a 2-fold increase of intracellular ceramide. As before, ceramide increase was abrogated by pre-incubation with the cyclic peptide. Because in cell lines, UV irradiation directly activates cell surface receptors such as Fas and the TNFα receptor, sham- or UV-irradiated MC were used to determine p75 activation. Within 30 minutes UV-irradiation substantially induced JNK activation that was partially decreased by NT-3 pre-treatment. These data demonstrate that in MC, increased cAMP levels decrease p75 upregulation and suggest that UV-irradiation may induce p75 expression at least in part by decreasing cellular cAMP. Furthermore, p75 is specifically activated by NGF, and not NT-3, indicating that in the absence of trk A, p75 can signal alone in MC.

EXAMPLE 21 p75 Neurotrophin Receptor in the Control of Apoptosis-driven Hair Follicle Regression: Catagen Retardation in p75 NTR Knockout Mice and After p75 NTR Blockade by Cyclic Peptides Neurotrophins are involved in the control of apoptosis-driven hair follicle (HF) regression (catagen). In order to examine the role of $p75^{NTR}$, implicated in apoptosis control, the expression and function of $p75^{NTR}$ during spontaneous catagen development was studied in murine skin. Using immunohistochemistry, it was determined that $p75^{NTR}$ alone is strongly expressed in keratinocytes (KC) of the regressing outer root sheath, but both $p75^{NTR}$ and trkB and/or trkC are expressed by the non-regressing secondary hair germ KC. Because $p75^{NTR}$ signals for apoptosis when activated alone, but instead for survival when activated together with receptors of the trk family, the correlation between HF KC apoptosis and $p75^{NTR}$/trk expression was examined. TUNEL+HF KC expressed only the $p75^{NTR}$, while the surviving secondary hair germ keratinocytes expressed in addition trk receptors. To determine if $p75^{NTR}$ is functionally involved in catagen control, spontaneous catagen development was compared in vivo between $p75^{NTR}$ knockout (−/−) and age-matched wild type mice. There was a significant catagen retardation by 12% in $p75^{NTR}$ knockout mice as compared to wild type controls (p>0.05). To further examine the role of $p75^{NTR}$ in catagen development of C57BL/6 mice, HF catagen organ cultures were supplemented with diluent alone or with cyclic peptides known to bind the $p75^{NTR}$ and previously shown to block apoptosis in other cell types that require $p75^{NTR}$ activation. Cyclic peptides (0.01–100 μM) significantly retard catagen development by 33% compared to vehicle control (p<0.05). These findings suggest that $p75^{NTR}$ signaling is involved in the control of KC apoptosis during catagen and that $p75^{NTR}$ antagonistic cyclic peptides may prove useful for the treatment of hair disorders that display premature entry into catagen (e.g. telogen effluvium, androgenetic alopecia, alopecia areata).

EQUIVALENTS

Those skilled in the art will recognize, or be able to ascertain using no more than routine experimentation, many equivalents these specific embodiments of the invention described herein. Such equivalents are intended to be encompassed by the following claims.

What is claimed is:

1. A method of maintaining or inducing hair color in a mammal, said method comprising inhibiting p75 nerve growth factor receptor-mediated apoptosis in epidermal melanocytes wherein the apoptosis is inhibited by contacting the melanocytes after injury to the skin or hair follicles, with an effective amount of a neurotrophin or a biologically active fragment thereof that binds to the p75 nerve growth factor receptor expressed on melanocytes.

2. A method of inducing or maintaining skin color in a vertebrate comprising inhibiting p75 nerve growth factor receptor-mediated apoptosis in epidermal melanocytes wherein apoptosis is inhibited by contacting the melanocytes, after injury to the skin or hair follicles, with an effective amount of a neurotrophin or a biologically active fragment thereof that binds to the p75 nerve growth factor receptor expressed on melanocytes.

3. The method of claim 1, wherein the neurotrophin is nerve growth factor, neurotrophin-3, neurotrophin 4/5 or brain-derived neurotrophic factor.

4. The method of claim 1 wherein the biologically active fragment is peptide comprising amino acid sequence lysine-glycine-alanine.

5. The method of claim 2, wherein the neurotrophin is nerve growth factor, neurotrophin-3, neurotrophin 4/5 or brain-derived neurotrophic factor.

6. The method of claim 2 wherein in the biologically active fragment is a peptide comprising amino acid sequence lysine-glycine-alanine.

7. A method of maintaining or inducing hair color in a mammal, said method comprising inhibiting p75 nerve growth factor receptor-mediated apoptosis in epidermal melanocytes wherein the apoptosis is inhibited by contacting the melanocytes after injury to the skin or hair follicles with an effective amount of a peptide selected from the group consisting of SEQ ID NO:4, SEQ ID NO:9, and SEQ ID NO:10.

8. A method of inducing or maintaining skin color in a vertebrate comprising inhibiting p75 nerve growth factor receptor-mediated apoptosis in epidermal melanocytes wherein apoptosis is inhibited by contacting the melanocytes after injury to the skin or hair follicles with an effective amount of a peptide selected from the group consisting of SEQ ID NO:4, SEQ ID NO:9, and SEQ ID NO:10.

* * * * *

UNITED STATES PATENT AND TRADEMARK OFFICE
CERTIFICATE OF CORRECTION

PATENT NO. : 6,867,179 B1
DATED : March 15, 2005
INVENTOR(S) : Barbara A. Gilchrest, Mina Yaar and Mark Eller It is certified that error appears in the above-identified patent and that said Letters Patent is hereby corrected as shown below:

Title page,
Item [63], Related U.S. Application Data, should read as follows:
-- Continuation of application No. PCT/US99/02362, filed on Feb. 3, 1999, which is a continuation-in-part of application No. 09/018,194, filed on Feb. 4, 1998, which is a continuation-in part of application No. 08/793,683, filed on Apr. 3, 1997, now abandoned, which is the U.S. National Phase of PCT/US95/10971, filed on Aug. 30, 1995, which is a continuation of 08/298,941, filed on Aug. 31, 1994, now Pat. No. 6,103,689. --

Column 1,
Line 8, delete "08/93,683" and substitute therefor -- 08/793,683 --.

Column 33,
Line 22, between "is" and "peptide" insert -- a --.

Column 34,
Line 4, between "wherein" and "the" delete "in".

Signed and Sealed this

Nineteenth Day of July, 2005

JON W. DUDAS
*Director of the United States Patent and Trademark Office*